US010933222B2

(12) United States Patent
Weitzner et al.

(10) Patent No.: US 10,933,222 B2
(45) Date of Patent: Mar. 2, 2021

(54) TISSUE RETRACTION SYSTEM FOR PERFORMING MINIMALLY INVASIVE PROCEDURES

(71) Applicant: BOSTON SCIENTIFIC SCIMED, INC., Maple Grove, MN (US)

(72) Inventors: Barry Weitzner, Acton, MA (US); Gary J. Leanna, Holden, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 55 days.

(21) Appl. No.: 16/209,247

(22) Filed: Dec. 4, 2018

(65) Prior Publication Data
US 2019/0167950 A1 Jun. 6, 2019

Related U.S. Application Data

(60) Provisional application No. 62/594,766, filed on Dec. 5, 2017.

(51) Int. Cl.
A61M 25/01 (2006.01)
A61B 1/00 (2006.01)
(Continued)

(52) U.S. Cl.
CPC ..... A61M 25/0138 (2013.01); A61B 1/00085 (2013.01); A61B 1/00087 (2013.01);
(Continued)

(58) Field of Classification Search
CPC ........... A61B 17/0218; A61B 1/00078; A61M 25/01; A61M 25/01102; A61M 25/0138; A61M 25/0144; A61M 2025/0163
See application file for complete search history.

(56) References Cited

U.S. PATENT DOCUMENTS 5,312,432 A 5/1994 Pingleton et al.
6,009,877 A * 1/2000 Edwards ................ A61B 18/00
128/898
(Continued)

FOREIGN PATENT DOCUMENTS

WO 2014200737 A1 12/2014

OTHER PUBLICATIONS

Roppenecker, "Entwicklung und Validierung eines generativ gefertigten Snake-Like Manipulators fur die minimal-invasive Chirurgie", Technische Universitat Munchen, 146 pages, Aug. 8, 2017, Retrieved from internet : <http://mediatum.ub.tum.de?id=1316337> [Retrieved Feb. 21, 2019]. pp. 7, 47, 62; Figures 31, 53, 56, 63-69, 92-97, 109.
(Continued)

Primary Examiner — Ellen C Hammond
(74) Attorney, Agent, or Firm — Kacvinsky Daisak Bluni PLLC

(57) ABSTRACT

A system for performing minimally invasive procedures in a body lumen may include a flexible catheter having a plurality of lumens including a main lumen configured to receive an endoscope and at least one tool lumen; a first working instrument slidably disposed within a first tool lumen of the at least one tool lumen; a plurality of support elements disposed at a distal end of the catheter, the plurality of support elements being configured to shift between delivery and expanded configurations, wherein in the expanded configuration, the plurality of support elements forms an expanded cage to reshape the body lumen and form a working space; wherein at least one of the plurality of support elements is a tubular shaft having an opening proximate the working space; and a filament extending through the tubular shaft to a clip disposed outside the opening, the clip being manipulatable by the first working instrument.

20 Claims, 13 Drawing Sheets

(51) Int. Cl.
*A61M 25/06* (2006.01)
*A61B 17/02* (2006.01)
*A61B 17/00* (2006.01)
*A61B 1/018* (2006.01)
*A61B 1/01* (2006.01)
*A61B 1/313* (2006.01)
*A61B 17/34* (2006.01)
*A61B 17/29* (2006.01)

(52) U.S. Cl.
CPC ...... *A61B 1/00098* (2013.01); *A61B 1/00135* (2013.01); *A61B 1/00154* (2013.01); *A61B 1/018* (2013.01); *A61B 17/00234* (2013.01); *A61B 17/0206* (2013.01); *A61B 17/0218* (2013.01); *A61M 25/0136* (2013.01); *A61M 25/0662* (2013.01); *A61B 1/01* (2013.01); *A61B 1/313* (2013.01); *A61B 17/29* (2013.01); *A61B 17/3423* (2013.01); *A61B 2017/003* (2013.01); *A61B 2017/0034* (2013.01); *A61B 2017/00269* (2013.01); *A61B 2017/00323* (2013.01); *A61B 2017/00349* (2013.01); *A61B 2017/00477* (2013.01); *A61B 2017/00818* (2013.01); *A61B 2017/0287* (2013.01)

(56) References Cited

U.S. PATENT DOCUMENTS

| | | | |
|---|---|---|---|
| 6,231,561 B1* | 5/2001 | Frazier | A61B 17/0401 604/500 |
| 6,423,058 B1* | 7/2002 | Edwards | A61B 18/12 606/41 |
| 7,025,756 B2 | 4/2006 | Frazier et al. | |
| 8,038,612 B2 | 10/2011 | Paz | |
| 8,075,481 B2 | 12/2011 | Park et al. | |
| 8,397,335 B2 | 3/2013 | Gordin et al. | |
| 8,945,155 B2 | 2/2015 | Gordin et al. | |
| 8,986,326 B2 | 3/2015 | Satake et al. | |
| 9,241,698 B2 | 1/2016 | Ransden et al. | |
| 9,463,003 B2 | 10/2016 | Gordin et al. | |
| 9,901,408 B2* | 2/2018 | Larkin | B25J 9/1671 |
| 10,143,459 B2 | 12/2018 | Heftman | |
| 2002/0123748 A1* | 9/2002 | Edwards | A61B 18/1477 606/41 |
| 2003/0225432 A1 | 12/2003 | Baptiste et al. | |
| 2004/0158263 A1* | 8/2004 | McAlister | A61B 17/068 606/139 |
| 2007/0142852 A1 | 6/2007 | Lee et al. | |
| 2008/0188868 A1* | 8/2008 | Weitzner | A61B 1/0014 606/130 |
| 2009/0312645 A1* | 12/2009 | Weitzner | A61B 1/00098 600/476 |
| 2011/0082347 A1 | 4/2011 | Okoniewski | |
| 2012/0271327 A1 | 10/2012 | West et al. | |
| 2013/0345519 A1 | 12/2013 | Piskun et al. | |
| 2015/0272564 A1* | 10/2015 | Piskun | A61B 17/00234 600/114 |
| 2015/0272762 A1* | 10/2015 | Cox | A61B 17/0401 606/207 |
| 2015/0327885 A1 | 11/2015 | Esanu | |
| 2019/0091444 A1* | 3/2019 | Melsheimer | A61M 25/0097 |
| 2020/0085284 A1* | 3/2020 | Piskun | A61B 17/0218 |

OTHER PUBLICATIONS

International Search Report and Written Opinion dated Mar. 4, 2019 for International Application No. PCT/US2018/063823.
Sakamoto, N., et al., "Endoscopic submucosal dissection of large colorectal tumors by using a novel spring-action S-O clip for traction (with video)", Gastrointestinal Endoscopy 69(7):1370-1374 (2009).
Fujii, T., et al., "A novel endoscopic suturing technique using a specially designed so-called "8-ring" in combination with resolution clips (with videos)", Gastrointestinal Endoscopy 66(6):1215-1220 (2007).
Matsumoto, K., et al., "T1594: A New Traction Device for Gastric Endoscopic Submucosal Dissecton (ESD): Two-Point Fixed by Latex Traction for Early Gastric Cancer", Gastrointestinal Endoscopy, 71(5):AB317 (2010).
Imaeda, H., et al., "Advanced endoscopic submucosal dissection with traction", World Journal of Gastrointestinal Endoscopy 6(7):286-295 (2014).
Sakamoto, N., et al.,"'Loop Clip' a new closure device for large mucosal defects after EMR and ESD", Endoscopy 40: E97-E98 (2008).
Fujihara, S., et al., "Management of a large mucosal defect after duodenal endoscopic resection", World Journal of Gastroenterology, 22(29):6595-6609 (2016).
Mori, H., et al., "The Loop Clip is Useful for Closing Large Mucosal Defects After Colorectal Endoscopic Submucosal Dissection: A Preliminary Clinical Study", Digestive Endoscopy 23:330-331 (2011).
Tsuji, K., et al., "Recent traction methods for endoscopic submucosal dissection", World Journal of Gastroenterology, 22(26):5917-5926 (2016).
Ritsuno, H., et al., "Prospective clinical trial of traction device-assisted endoscopic submucosal dissection of large superficial colorectal tumors using the S-O clip", Surgical Endoscopy 28:3143-3149 (2014).
Sakamoto, N., et al., "The facilitation of a new traction device (S-O clip) assisting endoscopic submucosal dissection for superficial colorectal neoplasms", Endoscopy, 40:E94-E95 (2008).
Takeda, T., et al., "Traction device to remove an adenoma in the appendiceal orifice by endoscopic submucosal dissection", Endoscopy 45:E239-E240 (2013).
Kato, M., et al., "Technical feasibility of line-assisted complete closure technique for large mucosal defects after colorectal endoscopic submucosal dissection", Endoscopy International Open, 5(1):E11-E16 (2017) DOI: http://dx.doi.org/10.1055/s-0042-121002.

* cited by examiner

TISSUE RETRACTION SYSTEM FOR PERFORMING MINIMALLY INVASIVE PROCEDURES

CROSS-REFERENCE TO RELATED APPLICATIONS

This application claims priority under 35 U.S.C. § 119 to U.S. Provisional Application Ser. No. 62/594,766, filed Dec. 5, 2017, the entirety of which is incorporated herein by reference.

TECHNICAL FIELD

The present disclosure pertains to medical devices and/or methods for manufacturing and/or using medical devices. More particularly, the present disclosure pertains to configurations of a system for performing minimally invasive procedures in a body lumen.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a system for performing minimally invasive procedures in a body lumen may comprise a flexible catheter having a plurality of lumens extending from a handle housing to a distal end of the flexible catheter. The plurality of lumens may include a main lumen configured to receive an endoscope, and at least one tool lumen. The system may comprise a first working instrument slidably disposed within a first tool lumen of the at least one tool lumen. The system may comprise a plurality of support elements disposed at the distal end of the flexible catheter, the plurality of support elements being configured to shift between a delivery configuration and an expanded configuration. In the expanded configuration, the plurality of support elements forms an expanded cage to reshape the body lumen and form a working space. At least one of the plurality of support elements is a tubular shaft having a lumen extending from the handle housing to an opening through a side wall of the tubular shaft proximate the working space. The system may comprise a filament extending through the lumen of the tubular shaft to a clip disposed outside the opening through the side wall of the tubular shaft, the clip being manipulatable by the first working instrument.

In addition or alternatively, and in a second aspect, the first working instrument includes a grasping tool.

In addition or alternatively, and in a third aspect, the clip is configured to releasably attach to tissue of the body lumen proximate the working space.

In addition or alternatively, and in a fourth aspect, tension applied to the filament retracts the tissue laterally relative to a central longitudinal axis of the flexible catheter.

In addition or alternatively, and in a fifth aspect, the system further comprises a tension-inducing element disposed at a proximal end of the filament.

In addition or alternatively, and in a sixth aspect, the tension-inducing element is a weight, a spring, or a pull tab.

In addition or alternatively, and in a seventh aspect, at least one of the plurality of support elements is a second tubular shaft having a lumen extending from the handle housing to an opening through a side wall of the second tubular shaft proximate the working space.

In addition or alternatively, and in an eighth aspect, the system further comprises a second filament extending through the lumen of the second tubular shaft to a second clip disposed outside the opening through the side wall of the second tubular shaft, the second clip being manipulatable by the first working instrument.

In addition or alternatively, and in a ninth aspect, the system further comprises a second working instrument slidably disposed within a second tool lumen of the at least one tool lumen.

In addition or alternatively, and in a tenth aspect, the first working instrument is configured to manipulate tissue of the body lumen proximate the working space.

In addition or alternatively, and in an eleventh aspect, a system for performing minimally invasive procedures in a body lumen may comprise a flexible catheter having a plurality of lumens extending from a handle housing to a distal end of the flexible catheter, the plurality of lumens including a main lumen configured to receive an endoscope. The system may comprise a first working instrument disposed within a first tool channel slidably disposed within a first tool lumen extending from the handle housing to the distal end of the flexible catheter. The system may comprise a plurality of support elements extending from the plurality of lumens at the distal end of the flexible catheter, the plurality of support elements being configured to shift between a delivery configuration and an expanded configuration. In the expanded configuration, the plurality of support elements forms an expanded cage to reshape the body lumen and form a working space. At least one of the plurality of support elements is a tubular shaft having a lumen extending from the handle housing to an opening through a side wall of the tubular shaft proximate the working space. The system may comprise a filament extending through the lumen of the tubular shaft to a clip disposed outside the opening through the side wall of the tubular shaft, the clip being manipulatable by the first working instrument to grasp tissue proximate the working space.

In addition or alternatively, and in a twelfth aspect, the first tool channel has a distal portion movable from a first position aligned with a longitudinal axis of the first tool lumen when the distal portion of the first tool channel is disposed within the first tool lumen to an angled position with respect to the longitudinal axis of the first tool lumen when the distal portion of the first tool channel is advanced out of the first tool lumen.

In addition or alternatively, and in a thirteenth aspect, when the distal portion of the first tool channel is in the angled position, the distal portion of the first tool channel includes a first curve extending in a first direction with respect to the longitudinal axis of the first tool lumen and a second curve extending in a second different direction with respect to the longitudinal axis of the first tool lumen.

In addition or alternatively, and in a fourteenth aspect, a distal end of the first tool channel opens laterally relative to the longitudinal axis of the first tool lumen when the distal portion of the first tool channel is in the angled position.

In addition or alternatively, and in a fifteenth aspect, the first tool channel is formed from a shape memory material and the distal portion is configured to assume the angled position when unconstrained by the first tool lumen.

In addition or alternatively, and in a sixteenth aspect, a system for performing minimally invasive procedures in a body lumen may comprise a flexible catheter having a plurality of lumens extending from a handle housing to a distal end of the flexible catheter, the plurality of lumens including a main lumen configured to receive an endoscope. The system may comprise a first working instrument disposed within a first tool channel slidably disposed within a first tool lumen extending from the handle housing to the distal end of the flexible catheter. The system may comprise a plurality of support elements extending from the plurality of lumens at the distal end of the flexible catheter, the plurality of support elements being configured to shift between a delivery configuration and an expanded configuration. In the expanded configuration, the plurality of support elements forms an expanded cage to reshape the body lumen and form a working space. At least one of the plurality of support elements is a tubular shaft having a lumen extending from the handle housing to an opening through a side wall of the tubular shaft proximate the working space. The system may comprise a filament extending through the lumen of the tubular shaft to a clip disposed outside the opening through the side wall of the tubular shaft, the clip being manipulatable by the first working instrument to grasp tissue proximate the working space. The opening through the side wall of the tubular shaft is a longitudinally-oriented slot, and the tubular shaft includes an outer tubular shaft slidably disposed over the tubular shaft such that the filament exits the lumen of the tubular shaft at a variable location along the longitudinally-oriented slot as determined by a distal end of the outer tubular shaft.

In addition or alternatively, and in a seventeenth aspect, at least one of the plurality of support elements is a second tubular shaft having a lumen extending from the handle housing to an opening through a side wall of the second tubular shaft proximate the working space.

In addition or alternatively, and in an eighteenth aspect, the system further comprises a second filament extending through the lumen of the second tubular shaft to a second clip disposed outside the opening through the side wall of the second tubular shaft, the second clip being manipulatable by the first working instrument.

In addition or alternatively, and in a nineteenth aspect, the opening through the side wall of the second tubular shaft is a second longitudinally-oriented slot, and the second tubular shaft includes a second outer tubular shaft slidably disposed over the second tubular shaft such that the filament exits the lumen of the second tubular shaft at a second variable location along the second longitudinally-oriented slot as determined by a distal end of the second outer tubular shaft.

In addition or alternatively, and in a twentieth aspect, the flexible catheter defines a central longitudinal axis, and the second variable location along the second longitudinally-oriented slot is located at a different axial position along the central longitudinal axis than the variable location along the longitudinally-oriented slot.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
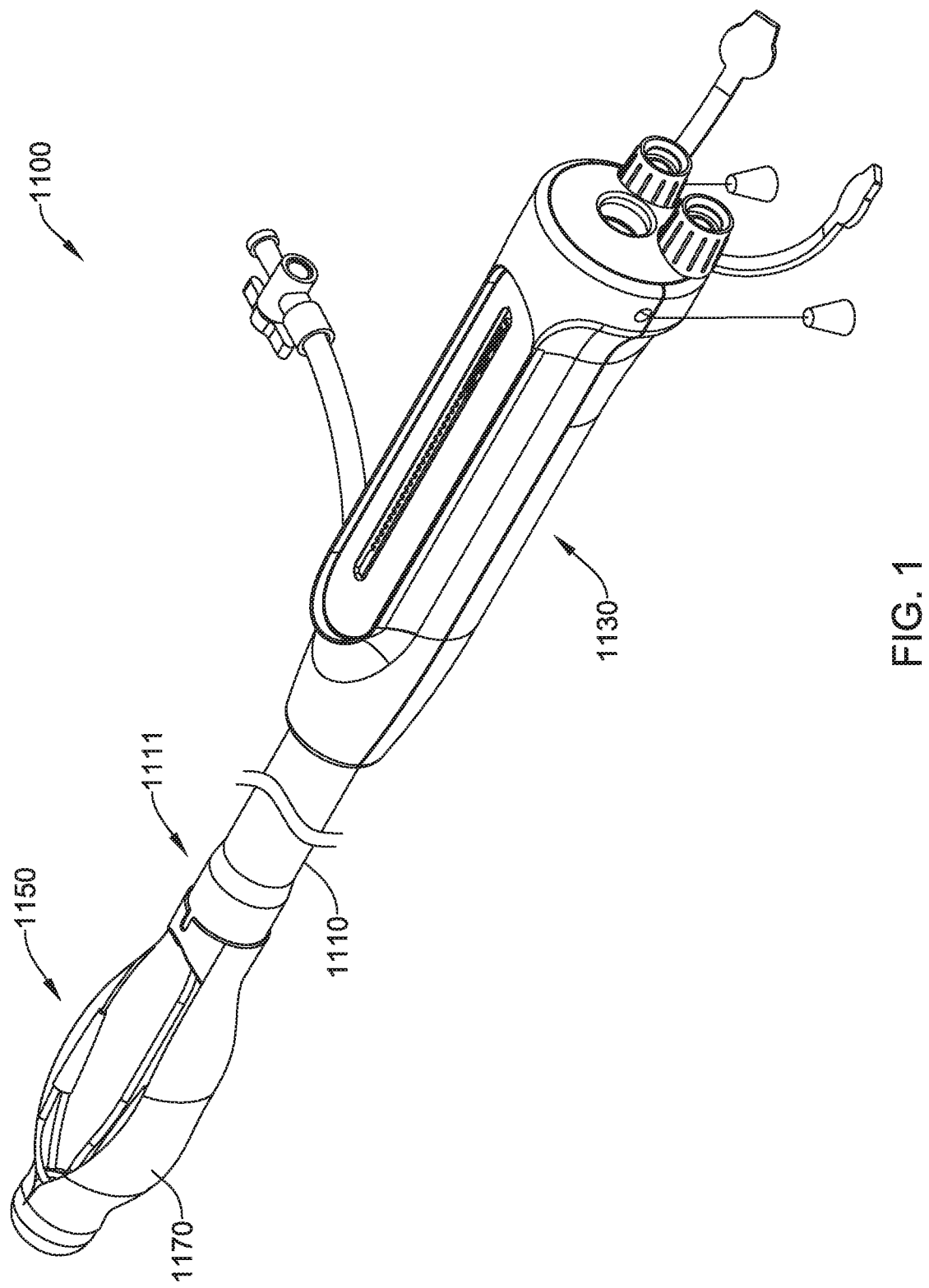
FIG. 1 illustrates aspects of an example system for performing minimally invasive procedures.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail herein. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to correspond to a measurement of a stated of identified dimension. The term "maximum extent" may be understood to mean a greatest measurement of a stated or identified dimension, while the term "minimum extent" may be understood to mean a smallest measurement of a stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, a "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described herein, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Endoscopic procedures involving the gastrointestinal system and/or other body lumens offer advantages over conventional surgery in that they are less invasive and may provide visualization. These procedures continue to evolve to address problems and provide new methods of treatment identified by those skilled in the art.

One current problem includes a lack of technology for an optimal minimally-invasive expansion of a working space in a body lumen adjacent to the target tissues that could otherwise collapse around the target tissue or defect during an operative treatment. Having the ability to effectively expand the working space in a body lumen could markedly facilitate an intra-luminal operation. An expanded working space in a body lumen allows the instruments and/or endoscope to be independently manipulated and properly visualized around the target tissue. One of skill would appreciate having the ability to see and approach both the target tissue and the surrounding anatomy for reference, orientation, and surgical maneuvering.

Disclosed herein are medical devices and/or systems that may be used within a portion of the gastrointestinal system and/or other body lumens in order to diagnose, treat, and/or repair the system. The devices and/or systems disclosed herein may also provide a number of additional desirable features and benefits as described in more detail herein. For the purpose of this disclosure, the discussion herein is directed toward treating gastrointestinal disorders endoscopically, and will be so described in the interest of brevity. This, however, is not intended to be limiting as the skilled person will recognize that the following discussion may also apply to other types of procedures and/or body lumens with no or minimal changes to the structure and/or scope of the disclosure.

The system(s) may include an endoscopic surgical suite that is created by the systems disclosed herein. The surgical suite may have a reversibly-expandable retractor and tool channels (or surgical tools and instruments) that may have a double curved configuration which maximize the distance from the surgical tools and working instruments to a target tissue to thereby maximize space for one or more surgical tools and instruments, and/or an endoscope, to each be maneuvered independently to visualize the target tissue and treat the target tissue from outside the patient in a minimally invasive manner. Embodiments taught herein can provide, among other improvements, an increase in distance between tool ports and the target tissue to enhance the independent maneuverability and triangulation of each of the tools with respect to the target tissue. This increase in distance can also provide a way of obtaining a larger field of view. The systems taught herein, for example, can: (i) enable a working space to be configured around the target tissue in tortuous body lumens and orifices such as the gastrointestinal tract using controls from outside the body; (ii) provide a flexible passageway for multiple surgical tools and instruments, such as an endoscope and grasper(s), to be passed from outside the body towards the target tissues; and (iii) organize and control the surgical tools and working instruments in the working space from outside the body.

In some embodiments, a catheter is placed over an articulating endoscope by inserting the articulating endoscope through a lumen of the catheter. In other embodiments, the catheter is placed over a flexible endoscope by backloading the catheter over the flexible endoscope, such as a conventional colonoscope. Then, the endoscope (e.g., colonoscope, etc.) is inserted to a position adjacent the target tissue and the catheter is advanced further over the flexible endoscope so the retractor is next to the target tissue.

In some embodiments, the surgical tools and working instruments for treating the target tissue are inserted directly through a respective tool lumen of a multi-lumen catheter. In these embodiments where the surgical tools and working instruments are inserted directly into the tool lumen(s) of the multi-lumen catheter, the surgical tools and working instruments can have a double curve at a distal end which can automatically assume a double curved position when exposed from the multi-lumen catheter so they curve away and then toward the target tissue, or alternatively, the surgical tools and working instruments can have a mechanism actively controlled by the user to articulate/angle the distal tip to obtain the first and/or second curve. In either case, the surgical tools and working instruments would have a double curved configuration to maximize space as described herein. In other embodiments, instead of the surgical tools and working instruments being inserted directly into the tool lumen(s) of the multi-lumen catheter, a tool channel may be inserted through the tool lumen(s) of the multi-lumen catheter and acts as a guide for the surgical tools and instruments. For example, the tool channel(s) may be first inserted into the tool lumen(s) of the multi-lumen catheter, and then the surgical tool(s) and instrument(s) may be inserted through the respective tool channel(s). The tool channel may have a double curve at a distal end which can automatically assume a double curved position when exposed from the multi-lumen catheter so it can curve away and then toward the target tissue, or alternatively, the tool channel can have a mechanism actively controlled by the user to articulate/angle the distal tip to obtain the first and/or second curve. In those embodiments utilizing the tool channel(s), the curving and maneuverability of the tool channel(s) control the positioning and orientation of the surgical tools and instruments, and therefore the surgical tools and working instruments need not be provided with a pre-curved tip or articulating mechanisms.

The double curve wherein the distal end of the tool channel(s) curves laterally away from a longitudinal axis of the tool lumen(s) in a first direction and then laterally toward, and in some embodiments past, the longitudinal axis of the tool lumen(s) in a second direction substantially opposite the first direction increases the distance from a distal opening at the distal end of the tool channel(s) to the target tissue as compared to a tool channel with a single curve curving from the longitudinal axis of the tool lumen toward the target tissue. This enhances access and maneuverability of the surgical tools and working instruments inserted through the tool channel(s). The same advantages may be obtained with surgical tools and working instruments having a double curve as compared to surgical tools and working instruments having a single curve.

The methods, devices, and systems taught herein can be used for minimally-invasive procedures which involves minimal access trauma and minimal collateral tissue damage during a surgical operation. Minimally-invasive surgery is desirable to reduce trauma to the patient, speed the healing process, reduce risk and, thus, reduce the length and expense of a hospital stay by minimizing or avoiding tissue damage, or risk of tissue damage. The systems disclosed herein may also enable triangulation to be achieved. Tissue triangulation, wherein the tissue is triangulated between two endoscopic working instruments, may enhance accessibility and maneuverability.

FIG. 1 illustrates aspects of a system 1100 for performing minimally invasive procedures in a body lumen. The system 1100 may include a flexible multi-lumen catheter 1110 having a plurality of lumens extending from a handle housing 1130 to a distal end 1111 of the flexible multi-lumen catheter 1110. The system 1100 may also include a retractor system 1150 positioned at the distal end 1111 of the flexible multi-lumen catheter 1110. In some embodiments, the retractor system 1150 may include a cover 1170 secured to the distal end 1111 of the flexible multi-lumen catheter 1110. Some suitable but non-limiting materials for the flexible multi-lumen catheter 1110, the handle housing 1130, the retractor system 1150, and/or the cover 1170, for example metallic materials, polymer materials, composite materials, etc., are described herein. Additional details regarding various aspects of these elements and/or features is described herein.

Figure 2:
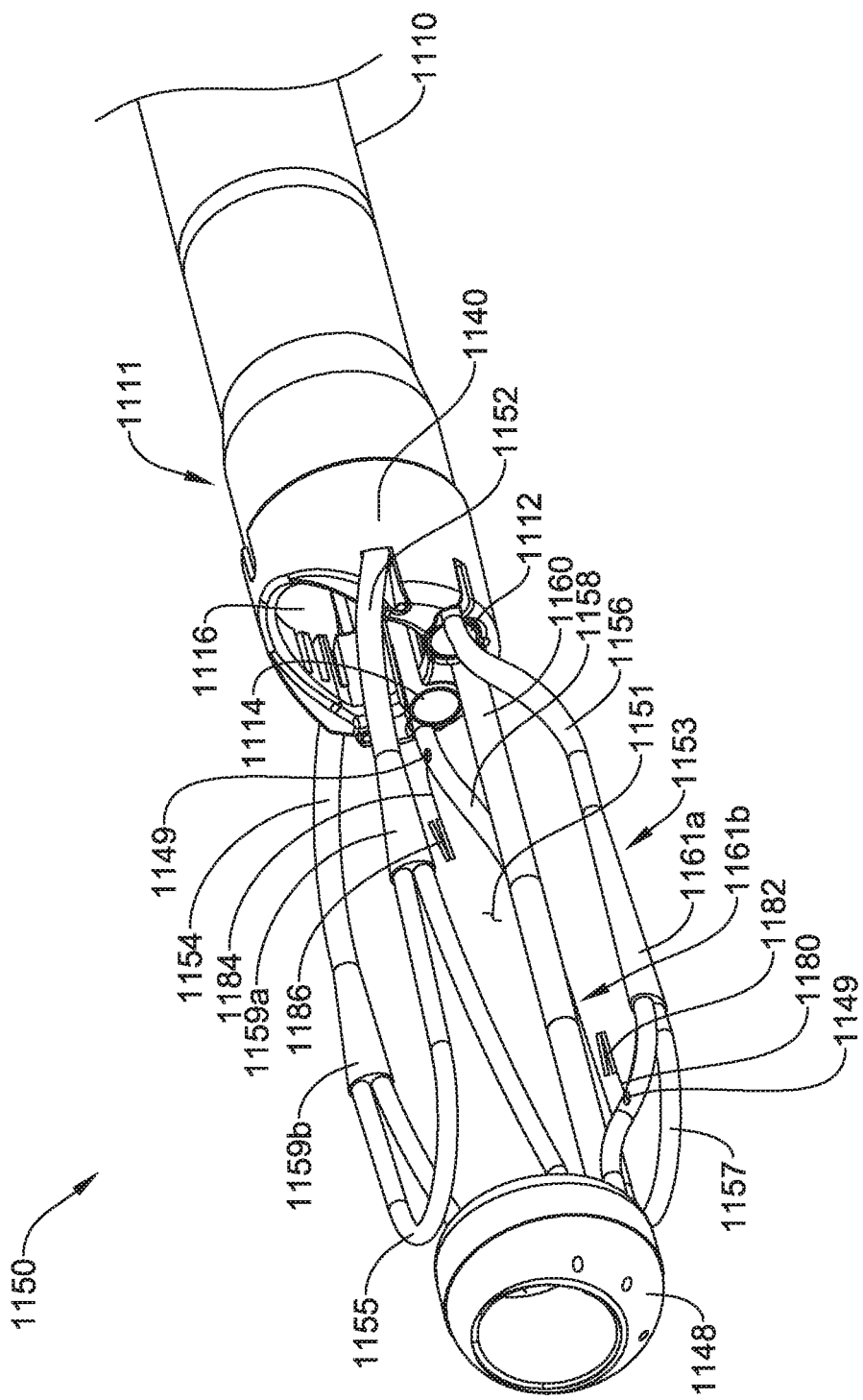
FIG. 2 illustrates aspects of an example expandable structure in a collapsed delivery configuration.
Figure 3:
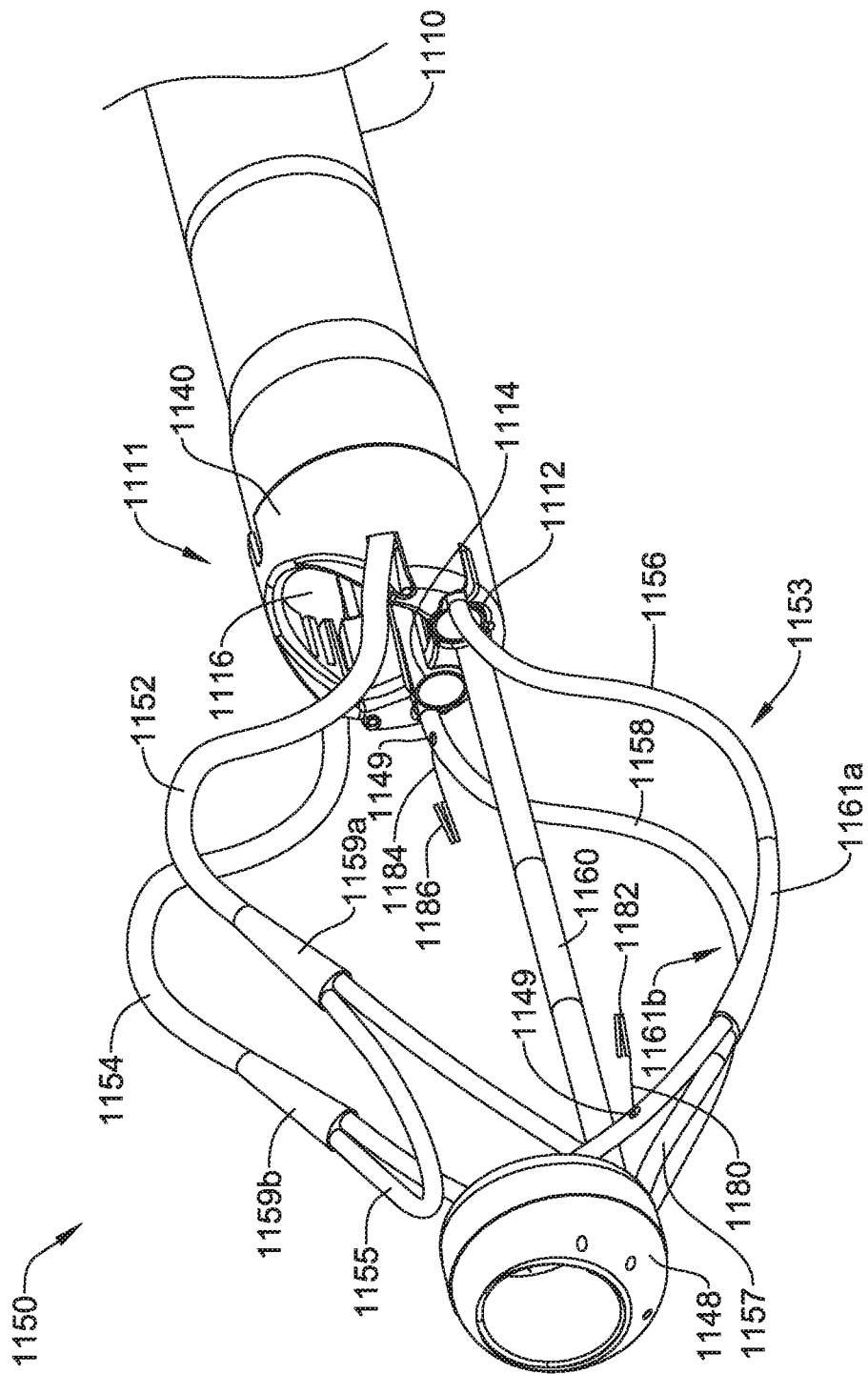
FIG. 3 illustrates aspects of the example expandable structure of FIG. 2 in an expanded configuration.

FIGS. 2 and 3 illustrate selected aspects of the system 1100, generally focusing on the retractor system 1150 positioned at the distal end 1111 of the flexible multi-lumen catheter 1110. As mentioned herein, the flexible multi-lumen catheter 1110 may have a plurality of lumens extending from the handle housing 1130 to the distal end 1111 of the flexible multi-lumen catheter 1110. The plurality of lumens may include a main lumen 1116 configured and dimensioned to receive an endoscope, and at least one tool lumen configured to receive one or more tool channels and/or working instruments. In some embodiments, the at least one tool lumen may include a first tool lumen 1112 and a second tool lumen 1114. In some embodiments, one or more additional tool lumens may be provided.

In some embodiments, the main lumen 1116 may be configured and dimensioned to receive a conventional endoscope (e.g., a colonoscope, etc.), and the flexible multi-lumen catheter 1110 may be backloaded over the endoscope. In some embodiments, the main lumen 1116 may be configured and dimensioned to receive an articulating endoscope. Moreover, in some embodiments, the endoscope may be inserted into the main lumen 1116 of the flexible multi-lumen catheter 1110 and advanced and/or inserted through the main lumen 1116 of the flexible multi-lumen catheter 1110 into the body lumen. In at least some embodiments, the main lumen 1116 may be accessible at a proximal end of the handle housing 1130.

Turning now to the retractor system 1150, which forms a body lumen reshaping or reconfiguring system, the retractor system 1150 is positioned at the distal end 1111 of the flexible multi-lumen catheter 1110. The retractor system 1150 includes a plurality of support elements 1153 disposed at the distal end 1111 of the flexible multi-lumen catheter 1110, wherein in at least some embodiments, the plurality of support elements 1153 may include a first support element 1152, a second support element 1154, a third support element 1156, and a fourth support element 1158. In some embodiments, the plurality of support elements 1153 may include two support elements, three support elements, four support element, five support elements, six support elements, etc. The plurality of support elements 1153 is configured to form an expanded cage to reshape the body lumen and form a working space 1151 within the body lumen to improve visibility, accessibility, and maneuverability within the working space 1151 and/or the expanded cage. In some embodiments, the working space 1151 may be substantially symmetrical, substantially asymmetrical, or a combination thereof. Some suitable but non-limiting materials for the first support element 1152, the second support element 1154, the third support element 1156, the fourth support element 1158, etc., for example metallic materials, polymer materials, composite materials, etc., are described herein.

The plurality of support elements 1153 may be configured to shift between a collapsed delivery configuration (e.g., FIG. 2), wherein the plurality of support elements 1153 generally does not extend radially and/or laterally outward beyond a transverse dimension or maximum outer extent of the distal end of the flexible multi-lumen catheter 1110, and an expanded configuration (e.g., FIG. 3), wherein the plurality of support elements 1153 extends radially and/or laterally outward beyond the transverse dimension or maximum outer extent of the distal end of the flexible multi-lumen catheter 1110. In the expanded configuration, the plurality of support elements 1153 may form the expanded cage to reshape the body lumen and form the working space 1151. In some embodiments, the plurality of support elements 1153 expands to both sides of a plane passing through a central longitudinal axis of the flexible multi-lumen catheter 1110.

In some embodiments, the plurality of support elements 1153 includes an upper bridge member 1155 extending laterally and/or transversely between the first support element 1152 and the second support element 1154 to add stability to the retractor system 1150 and maintain a desired orientation of the plurality of support elements 1153 during expansion. The upper bridge member 1155 may be attached to the first support element 1152 and the second support element 1154, for example, at an intermediate portion or position, to create a transverse structure limiting side-to side movement of the first support element 1152 and the second support element 1154. As shown, the upper bridge member 1155 may extend arcuately in a distal direction between the first support element 1152 and the second support element 1154. The upper bridge member 1155 may be a separate component attached to the first support element 1152 and the second support element 1154 by tubular elements 1159a and 1159b, respectively. In some embodiments, the tubular elements 1159a and 1159b may be formed from a heat shrink wrap or other suitable moldable material. Some suitable but non-limiting materials for the upper bridge member 1155, and the tubular elements 1159a and 1159b, for example metallic materials, polymer materials, composite materials, etc., are described herein.

In some embodiments, the tubular elements 1159a and 1159b each have a first opening to receive the respective support element and a second opening to receive an end of the upper bridge member 1155 (e.g., FIGS. 2-3). In some examples, the tubular elements 1159a and 1159b may also "bulk up" or increase an outer diameter of the first support element 1152 and the second support element 1154. In some embodiments, the plurality of support elements 1153 (e.g., the first support element 1152, the second support element 1154, etc.) is about 0.035 inches in diameter (although other dimensions are contemplated). Other methods of attachment of the upper bridge member 1155 are also contemplated (e.g., adhesives, welding, etc.). Alternately, the upper bridge member 1155 may be integrally formed with one or both of the first support element 1152 and the second support element 1154. The upper bridge member 1155 can be composed of a material similar to the plurality of support elements 1153 or can be composed of a different material. In some embodiments, additional bridge members (not shown) may be provided between the first support element 1152 and the second support element 1154 to increase stability.

In some embodiments, the upper bridge member 1155 may extend generally parallel to the central longitudinal axis of the flexible multi-lumen catheter 1110 in the collapsed configuration, when viewed from a side of the system 1100 (e.g., a plane containing the upper bridge member 1155 may be generally parallel to the central longitudinal axis of the flexible multi-lumen catheter 1110). The upper bridge member 1155, in the expanded configuration, may shift radially outward and/or laterally away from the central longitudinal axis of the flexible multi-lumen catheter 1110 to extend distally away from the plurality of support elements 1153 (e.g., the first support element 1152, the second support element 1154, etc.) at an oblique angle to the central longitudinal axis of the flexible multi-lumen catheter 1110 (e.g., a plane containing the upper bridge member 1155 may be oriented at an oblique angle to the central longitudinal axis of the flexible multi-lumen catheter 1110).

In some embodiments, the plurality of support elements 1153 may include a lower bridge member 1157 extending laterally and/or transversely between the third support element 1156 and the fourth support element 1158 to add stability to the retractor system 1150 and maintain a desired orientation of the plurality of support elements 1153 during expansion. The lower bridge member 1157 may be attached to the third support element 1156 and the fourth support element 1158, for example, at an intermediate portion or position, to create a transverse structure limiting side-to side movement of the third support element 1156 and the fourth support element 1158. As shown, the lower bridge member 1157 may extend arcuately in a distal direction between the third support element 1156 and the fourth support element 1158. The lower bridge member 1157 may be a separate component attached to the third support element 1156 and the fourth support element 1158 by tubular elements 1161a and 1161b, respectively. In some embodiments, the tubular elements 1161a and 1161b may be formed from a heat shrink wrap or other suitable moldable material. Some suitable but non-limiting materials for the lower bridge member 1157, and the tubular elements 1161a and 1161b, for example metallic materials, polymer materials, composite materials, etc., are described herein.

In some embodiments, the tubular elements 1161a and 1161b each have a first opening to receive the respective support element and a second opening to receive an end of the lower bridge member 1157 (e.g., FIGS. 2-3). In some examples, the tubular elements 1161a and 1161b may also "bulk up" or increase an outer diameter of the third support element 1156 and the fourth support element 1158. In some embodiments, the plurality of support elements 1153 (e.g., the third support element 1156, the fourth support element 1158, etc.) is about 0.035 inches in diameter (although other dimensions are contemplated). Other methods of attachment of the lower bridge member 1157 are also contemplated (e.g., adhesives, welding, etc.). Alternately, the lower bridge member 1157 may be integrally formed with one or both of the third support element 1156 and the fourth support element 1158. The lower bridge member 1157 can be composed of a material similar to the plurality of support elements 1153 or can be composed of a different material. In some embodiments, additional bridge members (not shown) may be provided between the third support element 1156 and the fourth support element 1158 to increase stability.

In some embodiments, the lower bridge member 1157 may extend generally parallel to the central longitudinal axis of the flexible multi-lumen catheter 1110 in the collapsed configuration, when viewed from a side of the system 1100 (e.g., a plane containing the lower bridge member 1157 may be generally parallel to the central longitudinal axis of the flexible multi-lumen catheter 1110). The lower bridge member 1157, in the expanded configuration, may shift radially outward and/or laterally away from the central longitudinal axis of the flexible multi-lumen catheter 1110 to extend distally away from the plurality of support elements 1153 (e.g., the third support element 1156, the fourth support element 1158, etc.) at an oblique angle to the central longitudinal axis of the flexible multi-lumen catheter 1110 (e.g., a plane containing the lower bridge member 1157 may be oriented at an oblique angle to the central longitudinal axis of the flexible multi-lumen catheter 1110).

While the retractor system 1150 is illustrated with the upper bridge member 1155 and the lower bridge member 1157, the upper bridge member 1155 and the lower bridge member 1157 are not strictly necessary in some embodiments and may be considered as optional elements of the retractor system 1150.

The flexible multi-lumen catheter 1110 includes a proximal coupler cap 1140 fixedly attached at a distal end 1111 of the flexible multi-lumen catheter 1110, wherein the plurality of support elements 1153 extends through longitudinally-extending openings formed in the proximal coupler cap 1140. A distal end of each of the plurality of support elements 1153 may be fixedly secured to a distal coupler cap 1148. In at least some embodiments, the proximal coupler cap 1140 and/or the distal coupler cap 1148 may include a main lumen aperture sized and configured to permit an endoscope or other medical device to pass through the main lumen aperture. In some embodiments, the distal coupler cap 1148 may be axially moveable relative to the flexible multi-lumen catheter 1110 and/or the proximal coupler cap 1140. In some embodiments, the distal coupler cap 1148 may be axially fixed relative to the flexible multi-lumen catheter 1110 and/or the proximal coupler cap 1140. Some suitable but non-limiting materials for the proximal coupler cap 1140 and the distal coupler cap 1148, for example metallic materials, polymer materials, composite materials, etc., are described herein.

In some embodiments, one or more of the plurality of support elements 1153 may optionally have a crimp forming a flattened portion at a distal end thereof adjacent to the distal coupler cap 1148. This flattened portion may reduce the bending stiffness at the flattened portion so that the flattened portion acts like a hinge to create a more predictable direction of expansion. The flattened portion may also decrease the amount of force required to initiate the bending. Such a flattened portion may also be used with other elements disclosed herein.

In some embodiments, the retractor system 1150 may include a support beam 1160 extending distally from the distal end 1111 of the flexible multi-lumen catheter 1110 and/or the proximal coupler cap 1140 to the distal coupler cap 1148. In some embodiments, the support beam 1160 may be fixedly attached to the distal coupler cap 1148. In some embodiments, the support beam 1160 may be configured to support the retractor system 1150 and/or the plurality of support elements 1153, which helps to create a more stable expanded cage and/or working space 1151, as described herein. In at least some embodiments, the support beam 1160 may be axially and/or longitudinally slidable relative to the flexible multi-lumen catheter 1110 and/or the proximal coupler cap 1140.

In some embodiments, the support beam 1160 may be substantially stiffer than the plurality of support elements 1153. In other embodiments, the support beam 1160 may be relatively flexible and/or at least as flexible as the plurality of support elements 1153. In some embodiments, the support beam 1160 may be in the form of a tubular shaft having a lumen configured to slidably receive a stabilizing or rigidifying structure such as a rigid tube or rod to reversibly stiffen the support beam 1160 and/or at least a portion of the retractor system 1150. The stabilizing or rigidifying structure may be independently and/or selectively actuated into or out of the lumen of the support beam 1160 by movement of a stiffening actuator on and/or in the handle housing 1130 to change the rigidity and/or stiffness of the support beam 1160. In some embodiments, the stiffening actuator may be slidably mounted within a longitudinally extending slot of the handle housing 1130 and slidably disposed within a lumen of the flexible multi-lumen catheter 1110. For example, sliding the stabilizing or rigidifying structure distally within the support beam 1160 may stiffen the support beam 1160, while retracting the stabilizing or rigidifying structure proximally from the support beam 1160 may return the support beam 1160 to a more flexible state to aid in collapsing of the retractor system 1150 for withdrawal of the system 1100 from the patient and/or the treatment site. While the support beam 1160 is illustrated with a substantially round cross-section, other suitable cross-sectional shapes are also contemplated. In an alternate configuration, instead of advancing a stabilizing or rigidifying structure within the lumen of the support beam 1160, a tubular stabilizing or rigidifying structure may be advanced over the support beam 1160. Some suitable but non-limiting materials for the support beam 1160, and/or the stabilizing or rigidifying structure, for example metallic materials, polymer materials, composite materials, etc., are described herein.

In some embodiments, at least one of the plurality of support elements 1153 (e.g., the first support element 1152, the second support element 1154, the third support element 1156, the fourth support element 1158, etc.) may be a tubular shaft having a lumen extending from the handle housing 1130 to a respective opening 1149 through a side wall of the tubular shaft (e.g., the first support element 1152, the second support element 1154, the third support element 1156, the fourth support element 1158, etc.) proximate the working space 1151, as shown in FIGS. 2 and 3 for example. In some embodiments, some of the plurality of support elements 1153 may each be a tubular shaft having a lumen extending from the handle housing 1130 to a respective opening 1149 through a side wall of the tubular shaft (e.g., the first support element 1152, the second support element 1154, the third support element 1156, the fourth support element 1158, etc.) proximate the working space 1151. In some embodiments, each and/or all of the plurality of support elements 1153 may each be a tubular shaft having a lumen extending from the handle housing 1130 to a respective opening 1149 through a side wall of the tubular shaft (e.g., the first support element 1152, the second support element 1154, the third support element 1156, the fourth support element 1158, etc.) proximate the working space 1151. In some embodiments, at least one of the plurality of support elements 1153 (e.g., the second support element 1154, the third support element 1156, the fourth support element 1158, etc.) may be a second tubular shaft having a lumen extending from the handle housing 1130 to a respective opening 1149 through a side wall of the second tubular shaft (e.g., the first support element 1152, the second support element 1154, the third support element 1156, the fourth support element 1158, etc.) proximate the working space 1151.

In some embodiments, a longitudinal position of the opening 1149 through the side wall of the tubular shaft (e.g., the first support element 1152, the second support element 1154, the third support element 1156, the fourth support element 1158, etc.) may be disposed at a proximal portion of the retractor system 1150 and/or the tubular shaft (e.g., the first support element 1152, the second support element 1154, the third support element 1156, the fourth support element 1158, etc.) adjacent the distal end 1111 of the flexible multi-lumen catheter 1110 and/or the proximal coupler cap 1140. In some embodiments, the longitudinal position of the opening 1149 through the side wall of the tubular shaft (e.g., the first support element 1152, the second support element 1154, the third support element 1156, the fourth support element 1158, etc.) may be disposed at a distal portion of the retractor system 1150 and/or the tubular shaft (e.g., the first support element 1152, the second support element 1154, the third support element 1156, the fourth support element 1158, etc.) adjacent the distal coupler cap 1148. In some embodiments, the longitudinal position of the opening 1149 through the side wall of the tubular shaft (e.g., the first support element 1152, the second support element 1154, the third support element 1156, the fourth support element 1158, etc.) may be disposed at an intermediate portion of the retractor system 1150 and/or the tubular shaft (e.g., the first support element 1152, the second support element 1154, the third support element 1156, the fourth support element 1158, etc.). In some embodiments, the longitudinal position of the opening 1149 through the side wall of the tubular shaft (e.g., the first support element 1152, the second support element 1154, the third support element 1156, the fourth support element 1158, etc.) may vary along a length of the tubular shaft (e.g., the first support element 1152, the second support element 1154, the third support element 1156, the fourth support element 1158, etc.) and/or from one tubular shaft (e.g., the first support element 1152, the second support element 1154, the third support element 1156, the fourth support element 1158, etc.) to another tubular shaft (e.g., the first support element 1152, the second support element 1154, the third support element 1156, the fourth support element 1158, etc.).

In some embodiments, the system 1100 and/or the retractor system 1150 may include a filament 1180 extending through the lumen of the tubular shaft (of one tubular shaft, of more than one tubular shaft, or of each tubular shaft), through the opening 1149 and/or the side wall of the tubular shaft (e.g., the first support element 1152, the second support element 1154, the third support element 1156, the fourth support element 1158, etc.), to a clip 1182 disposed outside of the opening 1149 through the side wall of the tubular shaft (e.g., the first support element 1152, the second support element 1154, the third support element 1156, the fourth support element 1158, etc.). For example, the filament 1180 may extend through a lumen of the first support element 1152, the second support element 1154, the third support element 1156, the fourth support element 1158, etc. In the example illustrated in FIG. 3, the filament 1180 extends through a lumen of the third support element 1156. The filament 1180 may extend proximally to the handle housing 1130, wherein the filament 1180 may be configured to be manipulated (e.g., tensioned, etc.) by a user outside of the patient. In at least some embodiments, the clip 1182 may be manipulatable by a first working instrument, as described herein, within and/or adjacent to the working space 1151. In some embodiments, the clip 1182 may be configured to releasably attach to the target tissue (e.g., a polyp, etc.) of the body lumen proximate the working space 1151. In some embodiments, the clip 1182 may be biased toward a closed configuration or a gripping configuration. In some embodiments, the clip 1182 may be self-biased toward the closed configuration or the gripping configuration. In some embodiments, the clip 1182 may include a spring member configured to bias or self-bias the clip 1182 toward the closed configuration or the gripping configuration. In some embodiments, the clip 1182 may be formed from a shape memory material configured to bias or self-bias the clip 1182 toward the closed configuration or the gripping configuration. Other configurations are also contemplated.

In some embodiments, the system 1100 and/or the retractor system 1150 may include a second filament 1184 extending through the lumen of the second tubular shaft, through the opening 1149 and/or the side wall of the second tubular shaft, to a second clip 1186 disposed outside of the opening 1149 through the side wall of the second tubular shaft. For example, the second filament 1184 may extend through a lumen of the second support element 1154, the third support element 1156, the fourth support element 1158, etc. In the example illustrated in FIG. 3, the second filament 1184 extends through a lumen of the fourth support element 1158. The second filament 1184 may extend proximally to the handle housing 1130, wherein the second filament 1184 may be configured to be manipulated (e.g., tensioned, etc.) by a user outside of the patient. In at least some embodiments, the second clip 1186 may be manipulatable by the first working instrument, as described herein, within and/or adjacent to the working space 1151. In some embodiments, the second clip 1186 may be configured to releasably attach to the target tissue (e.g., a polyp, etc.) of the body lumen proximate the working space 1151. In some embodiments, the second clip 1186 may be biased toward a closed configuration or a gripping configuration. In some embodiments, the second clip 1186 may be self-biased toward the closed configuration or the gripping configuration. In some embodiments, the second clip 1186 may include a spring member configured to bias or self-bias the second clip 1186 toward the closed configuration or the gripping configuration. In some embodiments, the second clip 1186 may be formed from a shape memory material configured to bias or self-bias the second clip 1186 toward the closed configuration or the gripping configuration. Other configurations are also contemplated. Some suitable but non-limiting materials for the filament 1180, the clip 1182, the second filament 1184, and/or the second clip 1186, for example metallic materials, polymer materials, composite materials, etc., are described herein. Additional filaments and/or clips may be provided in connection and/or cooperation with other and/or additional support elements and/or tubular shafts as desired. For example, in some embodiments, multiple filaments may be connected to a single clip to provide multiple force vectors and/or directions of control over the movement of the filament(s) and clip(s).

Figure 3A:
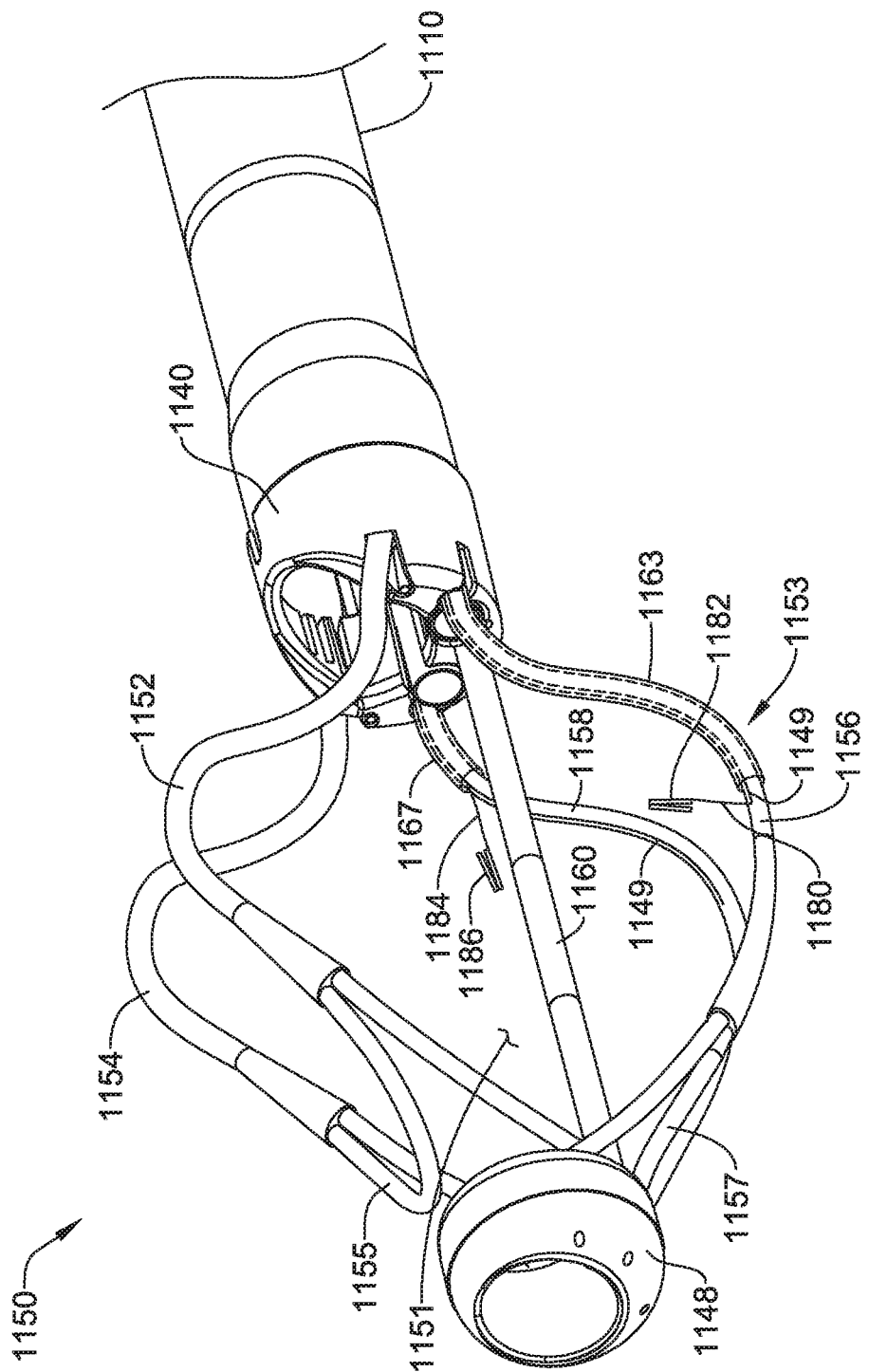
FIG. 3A illustrates additional and/or alternative aspects of the example expandable structure.

In some embodiments, as seen in FIG. 3A for example, the opening 1149 through the side wall of the tubular shaft (e.g., the first support element 1152, the second support element 1154, the third support element 1156, the fourth support element 1158, etc.) may be a longitudinally-oriented slot. In at least some of these embodiments, the retractor system 1150 and/or the tubular shaft (e.g., the first support element 1152, the second support element 1154, the third support element 1156, the fourth support element 1158, etc.) may include an outer tubular shaft 1163 slidably disposed over the tubular shaft (e.g., the first support element 1152, the second support element 1154, the third support element 1156, the fourth support element 1158, etc.) such that the filament 1180 exits the lumen of the tubular shaft (e.g., the first support element 1152, the second support element 1154, the third support element 1156, the fourth support element 1158, etc.) at a variable location and/or longitudinal position along the longitudinally-oriented slot (e.g., the opening 1149) as determined by a distal end of the outer tubular shaft 1163. The outer tubular shaft 1163 may be configured to slide along the tubular shaft (e.g., the first support element 1152, the second support element 1154, the third support element 1156, the fourth support element 1158, etc.) to vary the location and/or longitudinal position of the filament 1180 exiting the lumen of the tubular shaft (e.g., the first support element 1152, the second support element 1154, the third support element 1156, the fourth support element 1158, etc.), for example, to locate the clip 1182 closer to the target tissue (e.g., the polyp, etc.) and/or to change a force vector applied to the target tissue (e.g., the polyp, etc.) when the clip 1182 is attached to the target tissue (e.g., the polyp 20, etc.) and tension is applied to the filament 1180.

Additionally, in some embodiments, the opening 1149 through the side wall of the second tubular shaft (e.g., the first support element 1152, the second support element 1154, the third support element 1156, the fourth support element 1158, etc.) may be a second longitudinally-oriented slot. In at least some of these embodiments, the retractor system 1150 and/or the second tubular shaft (e.g., the first support element 1152, the second support element 1154, the third support element 1156, the fourth support element 1158, etc.) may include a second outer tubular shaft 1167 slidably disposed over the second tubular shaft (e.g., the first support element 1152, the second support element 1154, the third support element 1156, the fourth support element 1158, etc.) such that the second filament 1184 exits the lumen of the second tubular shaft (e.g., the first support element 1152, the second support element 1154, the third support element 1156, the fourth support element 1158, etc.) at a second variable location and/or longitudinal position along the longitudinally-oriented slot (e.g., the opening 1149) as determined by a distal end of the second outer tubular shaft 1167. The second outer tubular shaft 1167 may be configured to slide along the second tubular shaft (e.g., the first support element 1152, the second support element 1154, the third support element 1156, the fourth support element 1158, etc.) to vary the location and/or longitudinal position of the second filament 1184 exiting the lumen of the second tubular shaft (e.g., the first support element 1152, the second support element 1154, the third support element 1156, the fourth support element 1158, etc.), for example, to locate the second clip 1186 closer to the target tissue and/or to change a force vector applied to the target tissue when the second clip 1186 is attached to the target tissue (e.g., the polyp 20, etc.) and tension is applied to the second filament 1184.

In some embodiments, the second variable location, where the second filament 1184 exits the lumen of the second tubular shaft (e.g., the first support element 1152, the second support element 1154, the third support element 1156, the fourth support element 1158, etc.), along the second longitudinally-oriented slot is located and/or positioned at a different axial position along the central longitudinal axis of the flexible multi-lumen catheter 1110 than the variable location, where the filament 1180 exits the lumen of the tubular shaft (e.g., the first support element 1152, the second support element 1154, the third support element 1156, the fourth support element 1158, etc.), along the longitudinally-oriented slot is located and/or positioned. Further variation in location and/or longitudinal or axial position of the openings and/or locations where the filament(s) exit the tubular shaft(s) may be present in embodiments having additional tubular shafts, openings, filaments, and/or clips. For example, each opening and/or variable location where a filament exits a lumen may be located and/or positioned at a different axial position along the central longitudinal axis of the flexible multi-lumen catheter 1110. Some suitable but non-limiting materials for the outer tubular shaft 1163 and/or the second outer tubular shaft 1167, for example metallic materials, polymer materials, composite materials, etc., are described herein.

Figure 4:
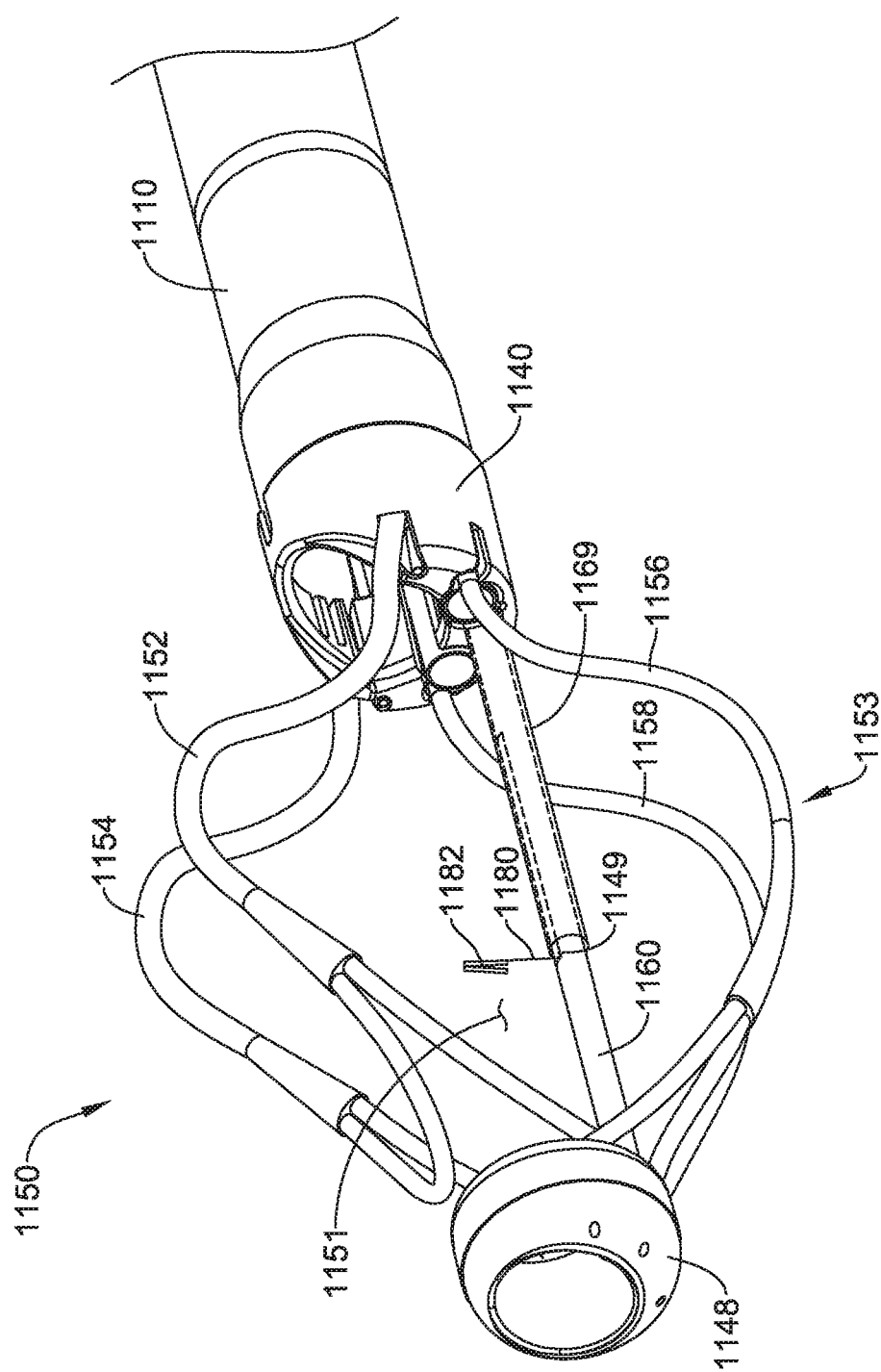
FIG. 4 illustrates additional and/or alternative aspects of the example expandable structure.

In some embodiments, the support beam 1160 may be a tubular shaft having a lumen extending from the handle housing 1130 to a respective opening 1149 through a side wall of the tubular shaft (e.g., the support beam 1160) proximate the working space 1151, as shown in FIG. 4 for example. In some embodiments, the opening 1149 may be a hole or aperture having a fixed size, location, and/or longitudinal position. In some embodiments, a longitudinal position of the opening 1149 through the side wall of the tubular shaft (e.g., the support beam 1160) may be disposed at a proximal portion of the retractor system 1150 and/or the tubular shaft (e.g., the support beam 1160) adjacent the distal end 1111 of the flexible multi-lumen catheter 1110 and/or the proximal coupler cap 1140. In some embodiments, the longitudinal position of the opening 1149 through the side wall of the tubular shaft (e.g., the support beam 1160) may be disposed at a distal portion of the retractor system 1150 and/or the tubular shaft (e.g., the support beam 1160) adjacent the distal coupler cap 1148. In some embodiments, the longitudinal position of the opening 1149 through the side wall of the tubular shaft (e.g., the support beam 1160) may be disposed at an intermediate portion of the retractor system 1150 and/or the tubular shaft (e.g., the support beam 1160). In some embodiments, the longitudinal position of the opening 1149 through the side wall of the tubular shaft (e.g., the support beam 1160) may vary along a length of the tubular shaft (e.g., the support beam 1160).

In some embodiments, the system 1100 and/or the retractor system 1150 may include a filament 1180 extending through the lumen of the tubular shaft (e.g., the support beam 1160), through the opening 1149 and/or the side wall of the tubular shaft (e.g., the support beam 1160), to a clip 1182 disposed outside of the opening 1149 through the side wall of the tubular shaft (e.g., the support beam 1160). For example, the filament 1180 may extend through a lumen of the support beam 1160. The filament 1180 may extend proximally to the handle housing 1130, wherein the filament 1180 may be configured to be manipulated (e.g., tensioned, etc.) by a user outside of the patient. In at least some embodiments, the clip 1182 may be manipulatable by a first working instrument, as described herein, within and/or adjacent to the working space 1151. In some embodiments, the clip 1182 may be configured to releasably attach to the target tissue (e.g., a polyp, etc.) of the body lumen proximate the working space 1151. In some embodiments, the clip 1182 may be biased toward a closed configuration or a gripping configuration. In some embodiments, the clip 1182 may be self-biased toward the closed configuration or the gripping configuration. In some embodiments, the clip 1182 may include a spring member configured to bias or self-bias the clip 1182 toward the closed configuration or the gripping configuration. In some embodiments, the clip 1182 may be formed from a shape memory material configured to bias or self-bias the clip 1182 toward the closed configuration or the gripping configuration. Other configurations are also contemplated.

In some embodiments, the opening 1149 through the side wall of the tubular shaft (e.g., the support beam 1160) may be a longitudinally-oriented slot. In at least some of these embodiments, the retractor system 1150 and/or the tubular shaft (e.g., the support beam 1160) may include an outer tubular shaft 1169 slidably disposed over the tubular shaft (e.g., the support beam 1160) such that the filament 1180 exits the lumen of the tubular shaft (e.g., the support beam 1160) at a variable location and/or longitudinal position along the longitudinally-oriented slot as determined by a distal end of the outer tubular shaft 1169. The outer tubular shaft 1169 may be configured to slide along the tubular shaft (e.g., the support beam 1160) to vary the location and/or longitudinal position of the filament 1180 exiting the lumen of the tubular shaft (e.g., the support beam 1160), for example, to locate the clip 1182 closer to the target tissue (e.g., the polyp, etc.) and/or to change a force vector applied to the target tissue (e.g., the polyp, etc.) when the clip 1182 is attached to the target tissue (e.g., the polyp, etc.) and tension is applied to the filament 1180.

In some embodiments, additional filaments may be provided through the support beam 1160 and additional clips may be provided at a distal end of the additional filaments. In some embodiments, the support beam 1160 may be a tubular shaft as described herein with respect to FIG. 4 in conjunction with at least one of the plurality of support elements 1153 being a tubular shaft having a lumen extending from the handle housing 1130 to a respective opening 1149 through a side wall of the tubular shaft proximate the working space 1151, as described herein with respect to FIGS. 2 and 3. Additional and/or other configurations and/or combinations of elements are also contemplated.

Figure 5:
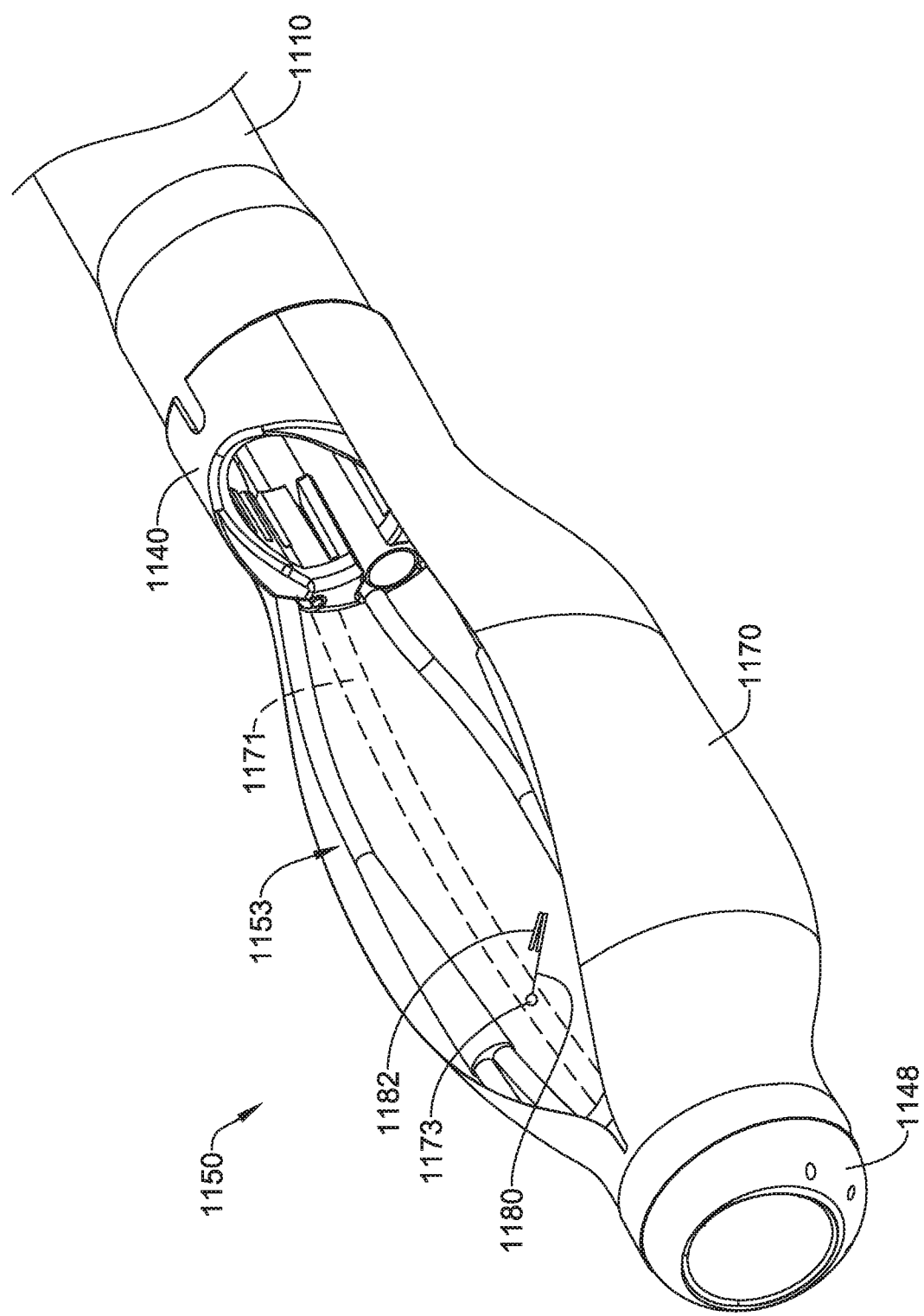
FIG. 5 illustrates additional and/or alternative aspects of the example expandable structure.

In some embodiments, the retractor system 1150 may include the cover 1170 secured to the distal end of the flexible multi-lumen catheter 1110, as seen in FIGS. 1 and 5. For the sake of clarity, the cover 1170 is omitted from the other Figures. As shown in FIG. 5, the cover 1170 may be mounted around and/or secured to a perimeter of the proximal coupler cap 1140 and/or the distal coupler cap 1148. In some embodiments, the cover 1170 may be pleated and/or sealed around the proximal coupler cap 1140 and/or the distal coupler cap 1148 by a heat shrink wrap. In some embodiments, the cover 1170 may be fixedly attached to the proximal coupler cap 1140 and/or the distal coupler cap 1148 by adhesives, welding, or other suitable means. In some embodiments, the cover 1170 may be integrally formed with the proximal coupler cap 1140 and/or the distal coupler cap 1148 as a single structure.

The cover 1170 may be positioned around the plurality of support elements 1153 in the collapsed delivery configuration, with an opening in the cover 1170 facing toward the target tissue (e.g., a lesion to be removed, the polyp, etc.). In the orientation(s) illustrated, the opening in the cover 1170 faces upwardly, but the orientation is not fixed or required and may be adjusted depending on the intended use of the system 1100. The cover 1170 can be configured to have the opening in the collapsed delivery configuration, or, alternatively, the cover 1170 may include a slit that can be opened by or due to stretching of the cover 1170 when the plurality of support elements 1153 is shifted to the expanded configuration. In some embodiments, when the plurality of support elements 1153 is shifted to the expanded configuration, the first support element 1152 and the second support element 1154 extend radially and/or laterally outward through the opening and/or the slit (e.g., past the cover 1170) toward the target tissue. Alternatively, in some embodiments, the cover 1170 can be attached to the plurality of support elements 1153 (e.g., the first support element 1152, the second support element 1154, the third support element 1156, and/or the fourth support element 1158, etc.) and thereby move with the plurality of support elements 1153 (e.g., the first support element 1152, the second support element 1154, the third support element 1156, and/or the fourth support element 1158, etc.).

When the target tissue is removed, the removed tissue is placed within the cover 1170 and the opening in the cover 1170 is closed by a suture or string, for example, to encapsulate the tissue and prevent leakage and seeding during removal from the body lumen. The suture or string may be embedded in a wall of the cover 1170, or in pockets or channels formed in the cover 1170, where the suture or string is permanently fixed at a distal anchor point and pulled proximally to tension the suture or string and close the opening in the cover 1170. The cover 1170 may provide a smooth and atraumatic surface for the delivery of the retractor system 1150 to the treatment site. The cover 1170 also helps to prevent unwanted tissue (e.g. walls of the body lumen, etc.) from entering the working space 1151 through the gaps between the support beam 1160 and/or the plurality of support elements 1153 during the surgical procedure.

With further reference to FIG. 5, in some embodiments, the cover 1170 may include a lumen 1171 formed within a side wall of the cover 1170 and extending distally from the distal end 1111 of the flexible multi-lumen catheter 1110 to a respective opening 1173 through a side wall of the cover 1170 proximate the working space 1151. In some embodiments, a longitudinal position of the opening 1173 through the side wall of the cover 1170 may be disposed at a proximal portion of the retractor system 1150 and/or the cover 1170 adjacent the distal end 1111 of the flexible multi-lumen catheter 1110 and/or the proximal coupler cap 1140. In some embodiments, the longitudinal position of the opening 1173 through the side wall of the cover 1170 may be disposed at a distal portion of the retractor system 1150 and/or the cover 1170 adjacent the distal coupler cap 1148.

In some embodiments, the longitudinal position of the opening 1173 through the side wall of the cover 1170 may be disposed at an intermediate portion of the retractor system 1150 and/or the cover 1170. Additionally, a circumferential location of the lumen 1171 within the side wall of the cover 1170 may be varied within the cover 1170. For example, in some embodiments, the lumen 1171 may be located at and/or adjacent an edge of the cover 1170 and/or an edge of the opening or slit in the cover 1170. In some embodiments, the lumen 1171 may be disposed substantially opposite the opening or slit in the cover 1170 with the opening 1173 of the lumen 1171 through the side wall of the cover 1170 facing towards the opening or slit in the cover 1170. In some embodiments, the lumen 1171 may be located at an intermediate and/or "side" circumferential location, as shown in FIG. 5 for example.

In some embodiments, the system 1100 and/or the retractor system 1150 may include a filament 1180 extending through the lumen of the cover 1170, through the opening 1173 and/or the side wall of the cover 1170, to a clip 1182 disposed outside of the opening 1173 through the side wall of the cover 1170. The filament 1180 may extend proximally to the handle housing 1130, wherein the filament 1180 may be configured to be manipulated (e.g., tensioned, etc.) by a user outside of the patient. In at least some embodiments, the clip 1182 may be manipulatable by a first working instrument, as described herein, within and/or adjacent to the working space 1151. In some embodiments, the clip 1182 may be configured to releasably attach to the target tissue (e.g., a polyp, etc.) of the body lumen proximate the working space 1151. In some embodiments, the clip 1182 may be biased toward a closed configuration or a gripping configuration. In some embodiments, the clip 1182 may be self-biased toward the closed configuration or the gripping configuration. In some embodiments, the clip 1182 may include a spring member configured to bias or self-bias the clip 1182 toward the closed configuration or the gripping configuration. In some embodiments, the clip 1182 may be formed from a shape memory material configured to bias or self-bias the clip 1182 toward the closed configuration or the gripping configuration. Other configurations are also contemplated.

In some embodiments, the system 1100 and/or the retractor system 1150 may include a second filament extending through a second lumen formed within the side wall of the cover 1170, through a second opening and/or the side wall of the cover 1170, to a second clip disposed outside of the second opening through the side wall of the cover 1170. The second filament may extend proximally to the handle housing 1130, wherein the second filament may be configured to be manipulated (e.g., tensioned, etc.) by a user outside of the patient. In at least some embodiments, the second clip may be manipulatable by the first working instrument, as described herein, within and/or adjacent to the working space 1151. In some embodiments, the second clip may be configured to releasably attach to the target tissue (e.g., a polyp, etc.) of the body lumen proximate the working space 1151. In some embodiments, the second clip may be biased toward a closed configuration or a gripping configuration. In some embodiments, the second clip may be self-biased toward the closed configuration or the gripping configuration. In some embodiments, the second clip may include a spring member configured to bias or self-bias the second clip toward the closed configuration or the gripping configuration. In some embodiments, the second clip may be formed from a shape memory material configured to bias or self-bias the second clip toward the closed configuration or the gripping configuration. Other configurations are also contemplated. Additional filaments and/or clips may be provided in connection and/or cooperation with other and/or additional lumens formed within the cover 1170 as desired.

Figure 6:
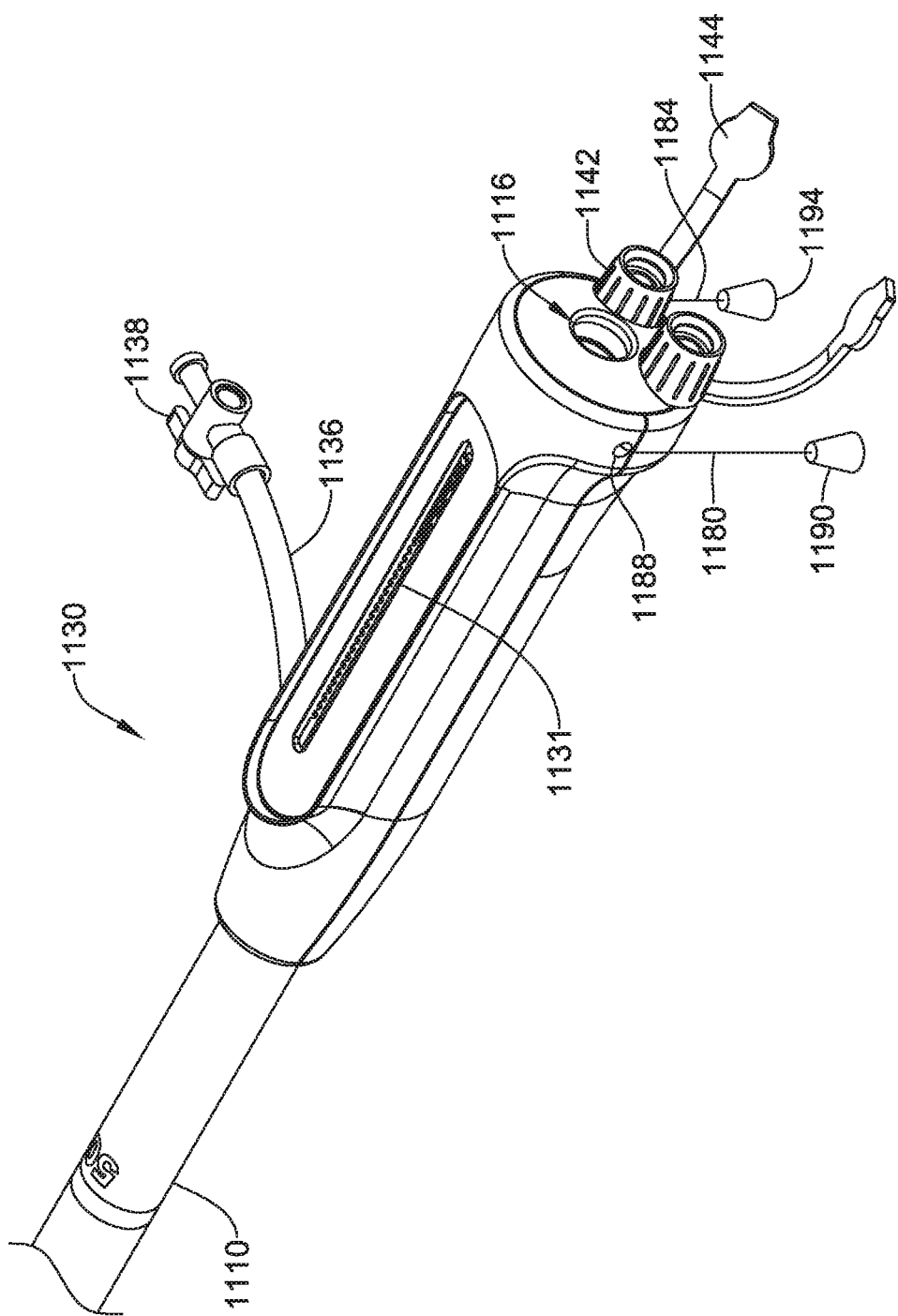
FIG. 6 illustrates aspects of an example handle of the system.

Turning to FIG. 6, the handle housing 1130 includes a longitudinally-oriented slot 1131 along which a retractor system actuator (not shown) may longitudinally slide. When the retractor system actuator is moved longitudinally along the longitudinally-oriented slot 1131, the plurality of support elements 1153 may be shifted between the collapsed delivery configuration and the expanded configuration. In some embodiments, the handle housing 1130 may include a plurality of teeth for engagement by a tooth coupled to or formed on the retractor system actuator, thereby forming a retaining or locking mechanism to retain the plurality of support elements 1153 in one of several selected positions. A release mechanism for the retaining or locking mechanism may be provided in some embodiments.

In some embodiments, the plurality of support elements 1153 may be coupled to the retractor system actuator within the handle housing 1130. In some embodiments, the retractor system actuator may be the stiffening actuator discussed herein. In some embodiments, the stiffening actuator may be separate and independent of the retractor system actuator, for separately controlling movement of the stabilizing or rigidifying structure, if provided. Longitudinal movement of the retractor system actuator relative to the handle housing 1130 may result in corresponding longitudinal movement of the plurality of support elements 1153. In some embodiments, proximal movement of the retractor system actuator relative to the handle housing 1130 may bring the distal coupler cap 1148 closer to the proximal coupler cap 1140, thereby causing the plurality of support elements 1153 to buckle outwards towards and/or into the expanded configuration. In some embodiments, distal movement of the retractor system actuator relative to the handle housing 1130 may move the distal coupler cap 1148 distally away from the proximal coupler cap 1140, thereby causing a proximal portion of the plurality of support elements 1153, which is disposed within the flexible multi-lumen catheter 1110 in the collapsed delivery configuration, to be extended out of the distal end 1111 of the flexible multi-lumen catheter 1110. The plurality of support elements 1153 may be self-biased and/or heat-set to move outwards towards and/or into the expanded configuration when unconstrained by the flexible multi-lumen catheter 1110. For example, the plurality of support elements 1153 may be formed from a shape memory material, such as nitinol or other suitable material, configured to return to a predetermined shape when outside biases and/or constraints are removed.

In some embodiments, the support beam 1160 may be coupled to the retractor system actuator within the handle housing 1130, wherein longitudinal movement of the retractor system actuator results in corresponding longitudinal movement and/or translation of the support beam 1160 relative to the handle housing 1130 and/or the proximal coupler cap 1140. In some embodiments, longitudinal movement and/or translation of the support beam 1160 relative to the handle housing 1130 and/or the proximal coupler cap 1140 may result in corresponding longitudinal movement and/or translation of the plurality of support elements 1153, thereby permitting the plurality of support elements 1153 to shift from the collapsed delivery configuration towards and/or into the expanded configuration. In some embodiments, longitudinal movement or translation of the distal coupler cap 1148 relative to the handle housing 1130 and/or the proximal coupler cap 1140 may cause and/or occur in conjunction with longitudinal movement or translation of the support beam 1160 relative to the handle housing 1130 and/or the proximal coupler cap 1140.

In some embodiments, the handle housing 1130 may include tubing 1136 having a one-way stopcock 1138 configured to provide an insufflation port in fluid communication with the main lumen 1116 of the flexible multi-lumen catheter 1110, which extends through the handle housing 1130 to a proximal end of the handle housing 1130. The insufflation port may be used to provide insufflation gas to the endoscope, or in some embodiments, to supplement insufflation gas provided by the endoscope. The insufflation gas may flow through the main lumen 1116 of the flexible multi-lumen catheter 1110 in the area around the endoscope since the cross-sectional dimension of the main lumen 1116 exceeds the cross-sectional dimension of the endoscope to leave a sufficient gap.

In some embodiments, the handle housing 1130 may include a proximal port 1142 in fluid communication with each of the at least one tool lumen (e.g., the first tool lumen 1112, the second tool lumen 1114, etc.) of the plurality of lumens extending through the flexible multi-lumen catheter 1110. Each proximal port 1142 may include a removable cover 1144 for sealing the proximal portion and/or the respective tool lumen against debris or contaminants. The removeable cover(s) 1144 may be removed from the proximal port(s) 1142 when access to the at least one tool lumen (e.g., the first tool lumen 1112, the second tool lumen 1114, etc.) is desired.

It may be appreciated that the handle housing 1130 can be any of a variety of shapes to provide a desired or ergonomic position for operation of the system 1100. By way of example, the retractor system actuator can be configured as a finger-activated button on the handle housing 1130 that slides back and forth within the longitudinally-oriented slot 1131 in the handle housing 1130 to expand or collapse the plurality of support elements 1153. A means for dynamically adjusting or ratcheting the position of the retractor system actuator can be provided along the longitudinally-oriented slot 1131 to lock the position of the retractor system actuator and/or the plurality of support elements 1153 in place when the retractor system actuator (e.g., the finger-activated button, etc.) is not pressed. In some embodiments, a button on the opposite side of the handle housing 1130 can be operatively connected to the support beam 1160 and/or the stabilizing or rigidifying structure to convert a flexible support beam 1160 into a rigid support beam 1160, or to convert the rigid support beam 1160 into a flexible support beam 1160.

At and/or adjacent to the proximal end of the handle housing 1130, the filament 1180 and/or the second filament 1184 may each extend through a respective aperture 1188 extending through a side wall of the handle housing 1130. In some embodiments, the system 1100 may further comprise a tension-inducing element disposed at a proximal end of each of the filament 1180 and/or the second filament 1184.

As shown in FIG. 6, in some embodiments, the tension-inducing element(s) may include a pull tab 1190 secured at the proximal end of the filament 1180 and/or a second pull tab 1194 secured at the proximal end of the second filament 1184. In some embodiments, the pull tab 1190 and/or the second pull tab 1194 may be configured to apply tension to the filament 1180 and/or the second filament 1184, respectively. For example, the pull tab 1190 and/or the second pull tab 1194 may be tensionable manually by a user. In some embodiments, the pull tab 1190 may be and/or include a weight secured to the proximal end of the filament 1180, wherein the weight may benefit from gravity to apply a constant tension to the filament 1180, in addition to being tensionable manually by a user. In some embodiments, the second pull tab 1194 may be and/or include a second weight secured to the proximal end of the second filament 1184, wherein the second weight may benefit from gravity to apply a constant tension to the second filament 1184, in addition to being tensionable manually by a user.

Figure 7:
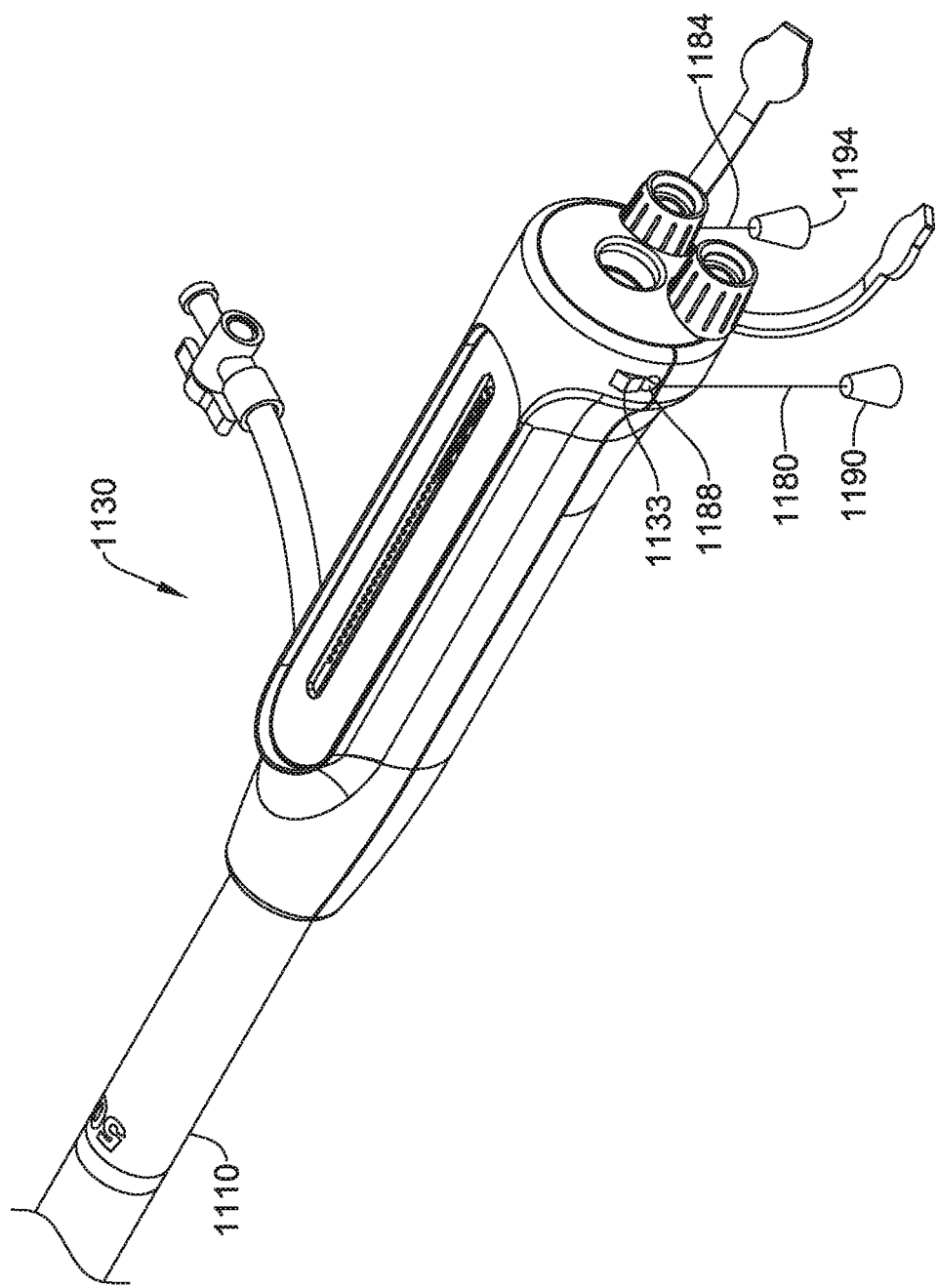
FIG. 7 illustrates additional and/or alternative aspects of the example handle.

In addition or alternatively, and as shown in FIG. 7, in some embodiments, the handle housing 1130 may include at least one locking mechanism 1133 configured to engage the filament 1180 and/or the second filament 1184 proximate the aperture(s) 1188 to lock the filament 1180 and/or the second filament 1184 relative to the handle housing 1130, thereby preventing relative longitudinal movement therebetween. In some embodiments, the at least one locking mechanism 1133 may be configured to slide along an outer surface of the handle housing 1130. In some embodiments, the at least one locking mechanism 1133 may be configured to slide circumferentially around the outer surface of the handle housing 1130. In some embodiments, the at least one locking mechanism 1133 may be configured to slide longitudinally and/or axially along the outer surface of the handle housing 1130. Other configurations are also contemplated—for example, a push button, or rotating movement of the at least one locking mechanism 1133 relative to the handle housing 1130.

Figure 8:
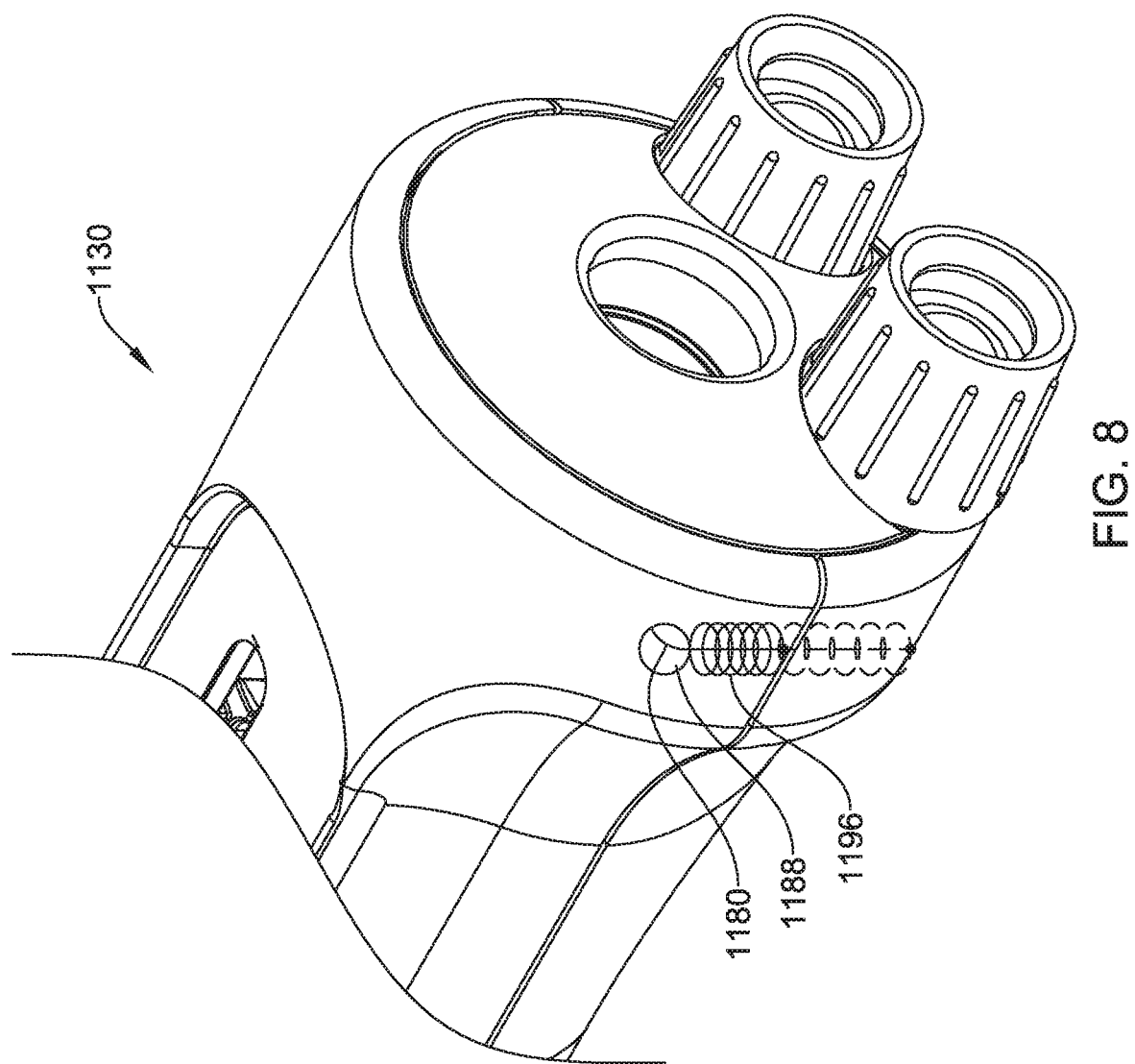
FIG. 8 illustrates additional and/or alternative aspects of the example handle.

In some embodiments, the tension-inducing element may include a spring 1196 secured to the proximal end of the filament 1180 proximate the aperture 1188 in the handle housing 1130, as seen in FIG. 8, and/or a second spring (not shown) secured to the proximal end of the second filament 1184. In at least some embodiments, the spring 1196 and/or the second spring may be a compression spring. In some embodiments, the spring 1196 and/or the second spring may engage the handle housing 1130 to automatically apply tension to the filament 1180 and/or the second filament 1184, respectively, when the spring 1196 and/or the second spring is under compression. In at least some embodiments, the spring 1196 and/or the second spring may be substantially extended and/or elongated (as shown in FIG. 8 in phantom lines) when the clip 1182 and/or the second clip 1186 is positioned at and/or adjacent to its respective opening 1149. As the clip 1182 and/or the second clip 1186 is pulled away from its respective opening 1149, the filament 1180 and/or the second filament 1184, respectively, is pulled and/or tensioned distally out the opening 1149 and thereby places the spring 1196 and/or the second spring in compression (as shown in FIG. 8 in solid lines). In some embodiments, the spring 1196 and/or the second spring may engage the outer surface of the handle housing 1130. In some embodiments, the spring 1196 and/or the second spring may be disposed within a recess and/or a slot formed within the handle housing 1130, and the spring 1196 and/or the second spring may engage a surface therein. Other configurations are also contemplated.

In some embodiments, the tension-inducing element may include the pull tab 1190 secured at the proximal end of the filament 1180 in conjunction with the spring 1196. For example, the filament 1180 may extend out of the aperture 1188, through the spring 1196, to the pull tab 1190, which may be spaced apart from the spring 1196 when the retractor system 1150 and/or the plurality of support elements 1153 is in the collapsed delivery configuration. As the clip 1182 (and the filament 1180) is pulled distally out of the opening 1149 to engage the target tissue (e.g., the polyp, etc.), the pull tab 1190 may be brought into contact and/or engagement with the spring 1196, thereby compressing the spring 1196 so at to apply tension to the filament 1180. In some embodiments, the tension-inducing element may include the second pull tab 1194 secured at the proximal end of the second filament 1184 in conjunction with the second spring. For example, the second filament 1184 may extend out of the aperture 1188, through the second spring, to the second pull tab 1194, which may be spaced apart from the second spring when the retractor system 1150 and/or the plurality of support elements 1153 is in the collapsed delivery configuration. As the second clip 1186 (and the second filament 1184) is pulled distally out of the opening 1149 to engage the target tissue (e.g., the polyp, etc.), the second pull tab 1194 may be brought into contact and/or engagement with the second spring, thereby compressing the second spring so at to apply tension to the second filament 1184.

Turning to FIGS. 9-12, use of the system 1100 will now be described with reference to removing a target tissue, such as a polyp 20, from a body lumen 10 (e.g., a colon, an intestine, a blood vessel, etc.), it being understood, however, that the system 1100 can be used for other procedures within the colon, the gastrointestinal tract, and/or other body lumens of the patient.

In some embodiments, a distal viewing endoscope, with the system 1100 backloaded over the proximal end of the endoscope, may be inserted through the body lumen 10 in a procedure to remove the target tissue (e.g., the polyp 20, etc.) from the wall of the body lumen 10. After placement of the endoscope adjacent the target issue (e.g., the polyp 20, etc.), the system 1100 may be advanced over the endoscope. The distal coupler cap 1148 may have an opening communicating with the main lumen 1116, and the proximal coupler cap 1140 may have an opening communicating with the main lumen 1116, of the flexible multi-lumen catheter 1110 to enable such backloading of the endoscope and advancement of the system 1100 thereover. In some embodiments, the system 1100 may be used without the benefit of an endoscope, as well.

Figure 9:
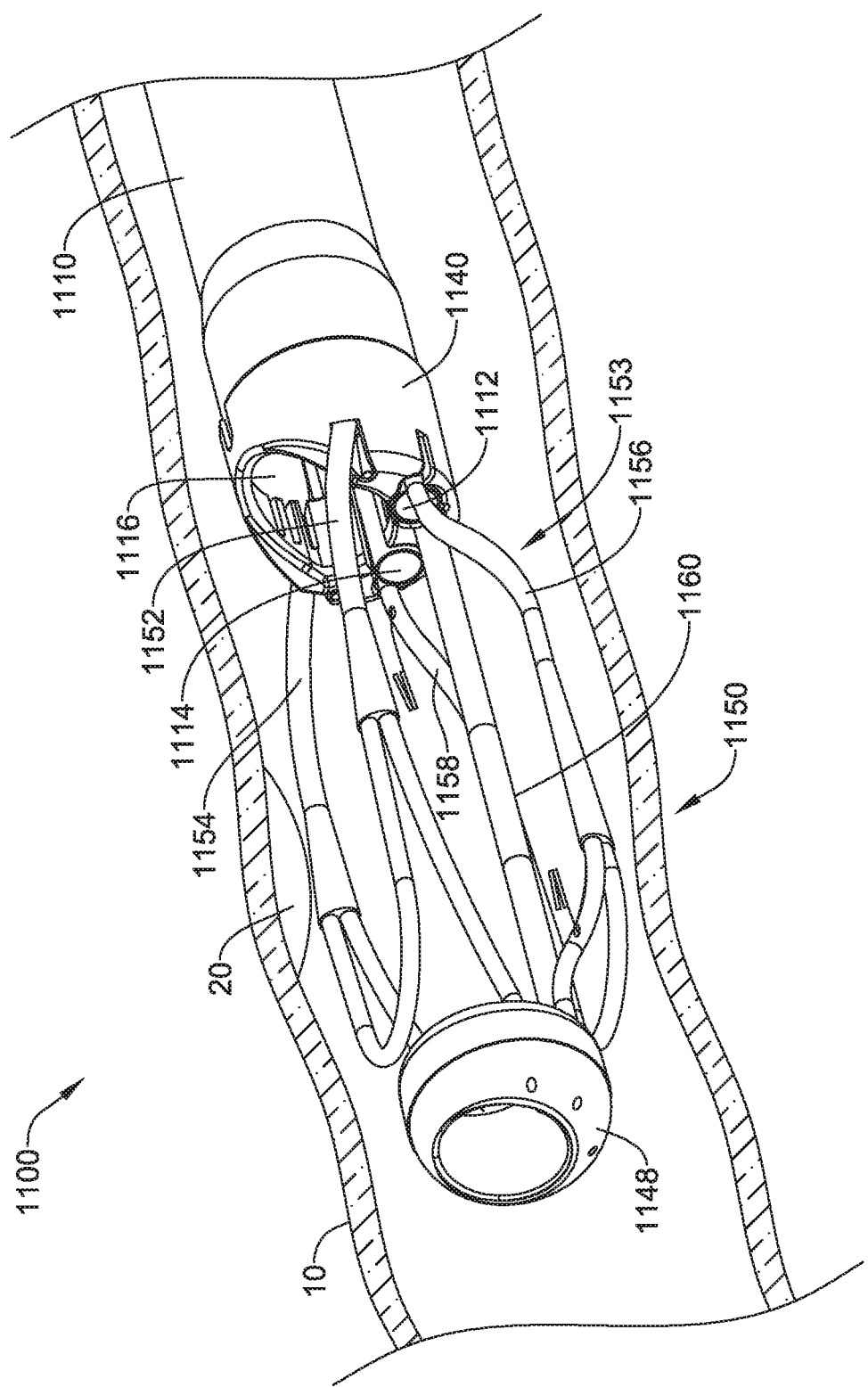
FIGS. 9-12 illustrate aspects of use of the system in a body lumen.

The flexible multi-lumen catheter 1110 may be advanced over the endoscope (not shown) until it reaches the target tissue (e.g., the polyp 20, etc.) and the retractor system 1150 is aligned with the target tissue (e.g., the polyp 20, etc.), as shown in FIG. 9 for example. As can be appreciated, in the collapsed delivery of the flexible multi-lumen catheter 1110 and/or the retractor system 1150, the plurality of support elements 1153 (e.g., the first support element 1152, the second support element 1154, the third support element 1156, the fourth support element 1158, etc.) may not exceed, or in some embodiments may only slightly exceed, the maximum transverse dimension or extent of the flexible multi-lumen catheter 1110. In the collapsed delivery configuration, the plurality of support elements 1153 is covered by the covering 1170 (not shown in FIG. 9 for clarity). In at least some embodiments, in the collapsed delivery configuration, the distal end of the endoscope is preferably positioned at the distal end of the proximal coupler cap 1140 and/or the main lumen 1116, and does not extend into the working space 1151 (e.g., FIG. 10) to thereby leave more room for maneuvering of the working instruments within the working space 1151 (e.g., FIG. 10). Other positions and/or configurations are also contemplated—e.g., in some embodiments, the endoscope may extend into the working space 1151 (e.g., FIG. 10).

Figure 10:
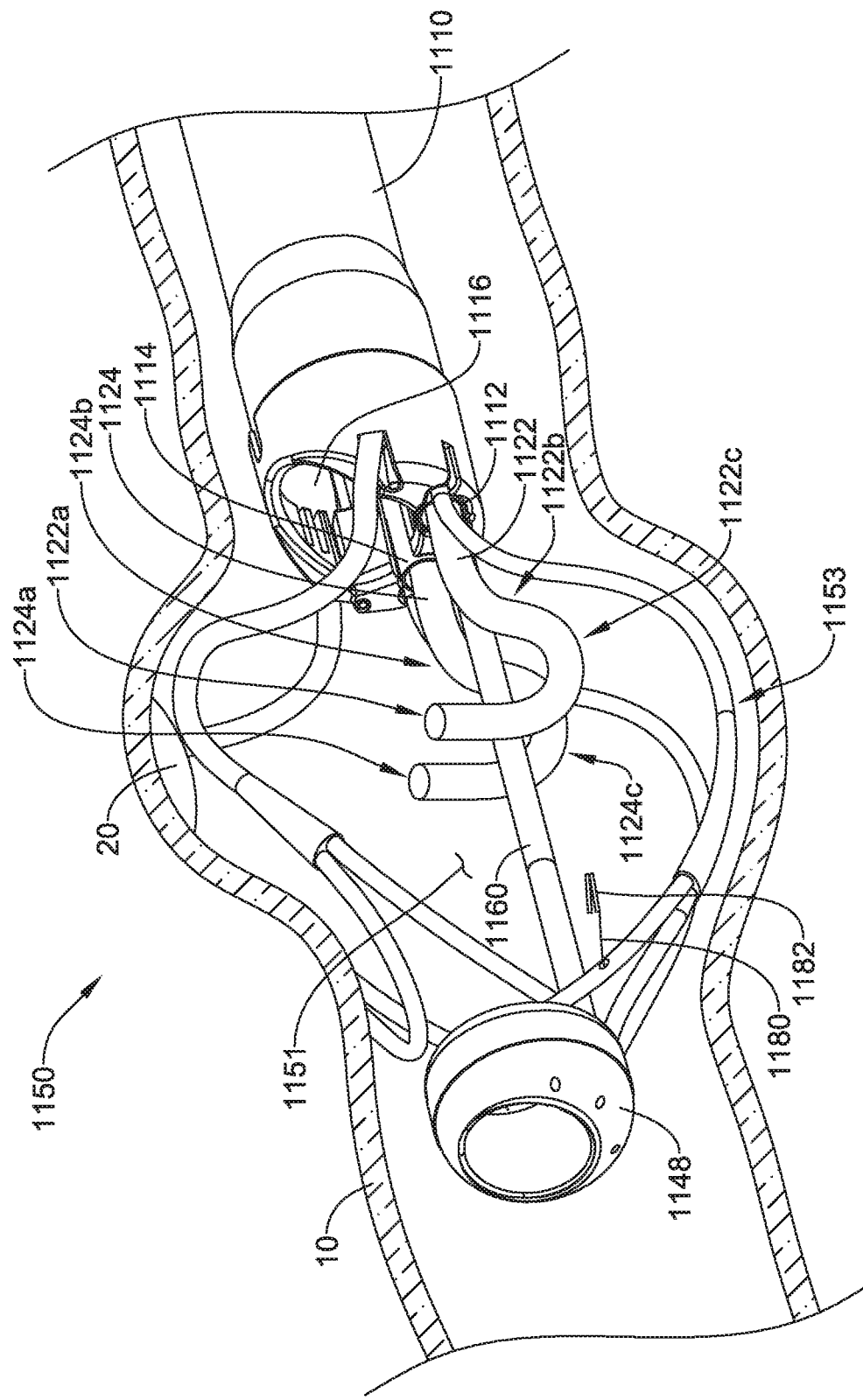

Next, the retractor system 1150 may be shifted to the expanded configuration within the body lumen 10 to form the working space 1151, as shown in FIG. 10 for example. As may be appreciated, shifting the retractor system 1150 to the expanded configuration may push walls of the body lumen 10 apart adjacent the target tissue (e.g., the polyp 20, etc.).

In embodiments having the stabilizing or rigidifying structure, the stabilizing or rigidifying structure may be optionally actuated (e.g., slidably translated distally, etc.) from a retracted position to a stiffening position within and/or over the support beam 1160. As discussed herein, a stiffening actuator at, in, and/or on the handle housing 1130 may be used to actuate the stabilizing or rigidifying structure. The stabilizing or rigidifying structure may be actuated before, during, or after shifting the retractor system 1150 to the expanded configuration, depending upon the particular configuration present in the system 1100.

Next, in some embodiments, at least one tool channel (e.g., a first tool channel 1122, a second tool channel 1124, etc.) may be inserted through the proximal port(s) 1142 at the proximal end of the handle housing 1130 (see FIG. 6) and advanced by the user through the at least one tool lumen (e.g., the first tool lumen 1112, the second tool lumen 1114, etc.) so they extend out the distal end of the at least one tool lumen (e.g., the first tool lumen 1112, the second tool lumen 1114, etc.) and into the working space 1151, as shown in FIG. 10. In some embodiments, the system 1100 may have at least one tool channel (e.g., a first tool channel 1122, a second tool channel 1124, etc.) pre-disposed within the at least one tool lumen (e.g., the first tool lumen 1112, the second tool lumen 1114, etc.) prior to advancing the flexible multi-lumen catheter 1110 over the endoscope and/or into the body lumen 10, and the at least one tool channel (e.g., a first tool channel 1122, a second tool channel 1124, etc.) may be subsequently advanced out the distal end of the at least one tool lumen (e.g., the first tool lumen 1112, the second tool lumen 1114, etc.) and into the working space 1151 following placement of the flexible multi-lumen catheter 1110 and shifting the retractor system 1150 and/or the plurality of support elements 1153 into the expanded configuration. While the system 1100 is generally described with two tool channels or working instruments, in some embodiments, only one tool channel or working instrument may be utilized, and in other embodiments, more than two tool channels or working instruments may be utilized, with the flexible multi-lumen catheter 1110 provided with a sufficient number of tool lumens.

Each of the at least one tool channel (e.g., the first tool channel 1122, the second tool channel 1124, etc.) has a lumen configured to receive a working instrument therethrough. As illustrated in FIG. 10, each of the at least one tool channel (e.g., the first tool channel 1122, the second tool channel 1124, etc.) may include a double curve at its respective distal tip (1122*a*, 1124*a*) defining a first curve (1122*b*, 1124*b*) extending away (downwardly as viewed in the figures) from the longitudinal axis of its respective tool lumen (e.g., the first tool lumen 1112, the second tool lumen 1114, etc.) and/or the target tissue (e.g., the polyp 20, etc.), and then transitioning into a second curve (1122*c*, 1124*c*) extending in a second opposite direction (upwardly as viewed in the figures) toward the longitudinal axis of its respective tool lumen (e.g., the first tool lumen 1112, the second tool lumen 1114, etc.) and the target tissue (e.g., the polyp 20, etc.). The first curve (1122*b*, 1124*b*) increases the distance from the distal tip (1122*a*, 1124*a*) of the at least one tool channel (e.g., the first tool channel 1122, the second tool channel 1124, etc.) to the target tissue (e.g., the polyp 20, etc.) as compared to a single curve which does not have a downward bend. The at least one tool channel (e.g., the first tool channel 1122, the second tool channel 1124, etc.) may be inserted through the proximal end of the flexible multi-lumen catheter 1110 and advanced through its respective tool lumen (e.g., the first tool lumen 1112, the second tool lumen 1114, etc.) in the flexible multi-lumen catheter 1110.

When the at least one tool channel (e.g., the first tool channel 1122, the second tool channel 1124, etc.) is inserted into its respective tool lumen (e.g., the first tool lumen 1112, the second tool lumen 1114, etc.) of the flexible multi-lumen catheter 1110, the pre-bent distal tip (1122a, 1124a) may be substantially straightened to facilitate advancement through the at least one tool lumen (e.g., the first tool lumen 1112, the second tool lumen 1114, etc.). When the at least one tool channel (e.g., the first tool channel 1122, the second tool channel 1124, etc.) has been advanced sufficiently distally so the distal tip (1122a, 1124a) is exposed from the at least one tool lumen (e.g., the first tool lumen 1112, the second tool lumen 1114, etc.), the distal tip (1122a, 1124a), returns to the pre-set double curved configuration.

For example, in some embodiments, the at least one tool channel (e.g., the first tool channel 1122, the second tool channel 1124, etc.) may have a distal portion movable from a first position aligned with a longitudinal axis of the at least one tool lumen (e.g., the first tool lumen 1112, the second tool lumen 1114, etc.) when the distal portion of the at least one tool channel (e.g., the first tool channel 1122, the second tool channel 1124, etc.) is disposed within the at least one tool lumen (e.g., the first tool lumen 1112, the second tool lumen 1114, etc.) to an angled position with respect to the longitudinal axis of the at least one tool lumen (e.g., the first tool lumen 1112, the second tool lumen 1114, etc.) when the distal portion of the at least one tool channel (e.g., the first tool channel 1122, the second tool channel 1124, etc.) is advanced out of the at least one tool lumen (e.g., the first tool lumen 1112, the second tool lumen 1114, etc.). In some embodiments, when the distal portion of the at least one tool channel (e.g., the first tool channel 1122, the second tool channel 1124, etc.) is in the angled position, the distal portion of the at least one tool channel (e.g., the first tool channel 1122, the second tool channel 1124, etc.) includes a first curve extending in a first direction with respect to the longitudinal axis of the at least one tool lumen (e.g., the first tool lumen 1112, the second tool lumen 1114, etc.) and a second curve extending in a second different direction with respect to the longitudinal axis of the at least one tool lumen (e.g., the first tool lumen 1112, the second tool lumen 1114, etc.). A distal end of the at least one tool channel (e.g., the first tool channel 1122, the second tool channel 1124, etc.) may open laterally relative to the longitudinal axis of the at least one tool lumen (e.g., the first tool lumen 1112, the second tool lumen 1114, etc.) when the distal portion of the at least one tool channel (e.g., the first tool channel 1122, the second tool channel 1124, etc.) is in the angled position.

In at least some embodiments, the at least one tool channel (e.g., the first tool channel 1122, the second tool channel 1124, etc.) can be composed of superelastic and/or shape memory material (e.g., nitinol, etc.), although other materials to provide the double curved configuration which returns from a substantially straight insertion shape to the double curved configuration when exposed can also be used, such as stainless steel. In some embodiments, the at least one tool channel (e.g., the first tool channel 1122, the second tool channel 1124, etc.) may be configured to assume the angled position when unconstrained by the at least one tool lumen (e.g., the first tool lumen 1112, the second tool lumen 1114, etc.). In some alternative embodiments, the at least one tool channel (e.g., the first tool channel 1122, the second tool channel 1124, etc.) may have a mechanism such as a pull wire which is actuated to bend its distal tip (1122a, 1124a). In some embodiments, the at least one tool channel (e.g., the first tool channel 1122, the second tool channel 1124, etc.) is unattached to the flexible multi-lumen catheter 1110 so that the user can freely control their axial movement from a proximal end portion during use. However, it is also contemplated that in alternate embodiments the at least one tool channel (e.g., the first tool channel 1122, the second tool channel 1124, etc.) can be attached to the flexible multi-lumen catheter 1110 (e.g., attached at proximal and/or distal ends to provide a floating tool channel).

The at least one tool channel (e.g., the first tool channel 1122, the second tool channel 1124, etc.) can optionally include markings at a region proximal to the flexible multi-lumen catheter 1110 to provide a visual indicator to the user of the depth of insertion of the at least one tool channel (e.g., the first tool channel 1122, the second tool channel 1124, etc.) through the at least one tool lumen (e.g., the first tool lumen 1112, the second tool lumen 1114, etc.). In some embodiments, the at least one tool channel (e.g., the first tool channel 1122, the second tool channel 1124, etc.) can have a luer fitting with a valve at the proximal end which can close off backflow of insufflation gas from the body lumen 10. This maintains insufflation when the working instrument is inserted through the at least one tool channel (e.g., the first tool channel 1122, the second tool channel 1124, etc.), as described herein. In some embodiments, the at least one tool channel (e.g., the first tool channel 1122, the second tool channel 1124, etc.) has a hemostatic valve connected at the proximal end of the at least one tool channel (e.g., the first tool channel 1122, the second tool channel 1124, etc.) to maintain insufflation during insertion of the working instrument. In some embodiments, the hemostatic valve may be disposed proximal of the luer fitting.

In some embodiments, the at least one tool channel (e.g., the first tool channel 1122, the second tool channel 1124, etc.) can be composed of a flexible soft material, such as a polymeric material. A superelastic nitinol backbone can in some embodiments be embedded in the wall of the polymeric material (e.g., within the double curved portion). Some suitable but non-limiting materials for the at least one tool channel (e.g., the first tool channel 1122, the second tool channel 1124, etc.), for example metallic materials, polymer materials, composite materials, etc., are described herein.

In some embodiments, the plurality of support elements 1153 may be shifted to the expanded configuration before inserting the at least one tool channel (e.g., the first tool channel 1122, the second tool channel 1124, etc.) into the working space 1151. In some embodiments, the at least one tool channel (e.g., the first tool channel 1122, the second tool channel 1124, etc.) may be inserted into the working space 1151 before the plurality of support elements 1153 is shifted to the expanded configuration. The at least one tool channel (e.g., the first tool channel 1122, the second tool channel 1124, etc.) may be independently rotated and/or moved axially to adjust its position within the working space 1151 and/or with respect to the target tissue (e.g., the polyp 20, etc.). As can be appreciated, relative terms such as upwardly and downwardly as used herein refer to the orientation of the system 1100 in the referenced Figures. If the position of the system 1100 and/or target tissue (e.g., the polyp 20, etc.) changes, the orientation and terms would also change.

Figure 11:
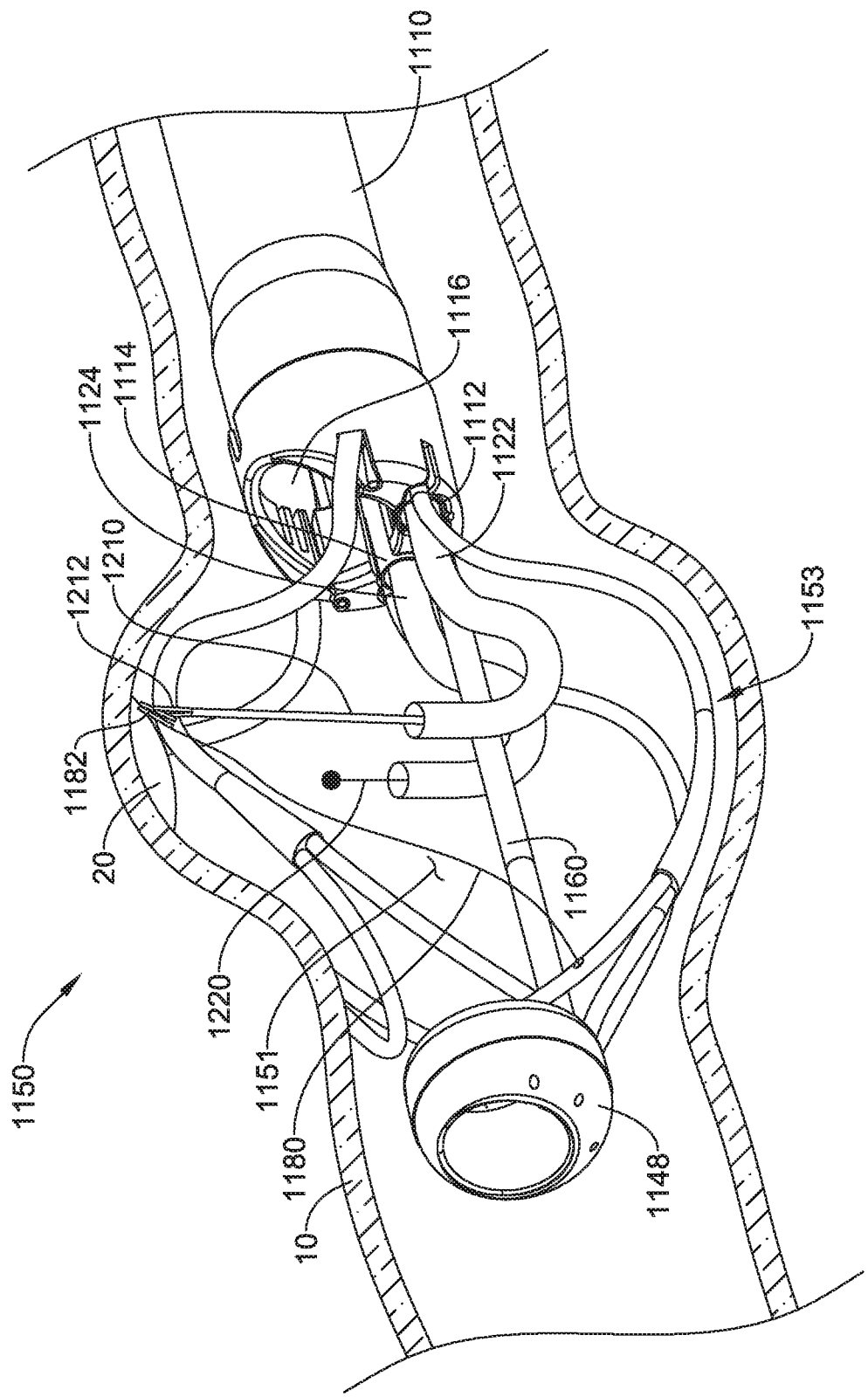

As shown in FIG. 11, in some embodiments, a first working instrument 1210 may be slidably disposed within and/or inserted through the at least one tool lumen (e.g., the first tool lumen 1112, the second tool lumen 1114, etc.) and/or the at least one tool channel (e.g., the first tool channel 1122, the second tool channel 1124, etc.) and advanced into the working space 1151. In some embodiments, the first working instrument 1210 may include a grasping tool 1212 configured to grasp tissue and/or manipulate other elements of the system 1100 such as, but not limited to, the clip 1182 and/or the second clip 1186. In some embodiments, the first working instrument 1210 may extend from the first tool lumen 1112 and/or the distal tip 1122*a* of the first tool channel 1122, following the double curve of the first tool channel 1122.

In some embodiments, a second working instrument 1220 may be slidably disposed within and/or inserted through the at least one tool lumen (e.g., the first tool lumen 1112, the second tool lumen 1114, etc.) and/or the at least one tool channel (e.g., the first tool channel 1122, the second tool channel 1124, etc.) and advanced into the working space 1151. In some embodiments, the second working instrument 1220 may include a resection tool, an ablation tool, an electrical cauterization tool, or other suitable working instrument depending on the intended use. In some embodiments, the second working instrument 1220 may extends from the second tool lumen 1114 and/or the distal tip 1124*a* of the second tool channel 1124, following the double curve of the second tool channel 1124.

In some embodiments, the first working instrument 1210 and/or the second working instrument 1220 may have the double curve described herein with respect to the at least one tool channel (e.g., the first tool channel 1122, the second tool channel 1124, etc.). In some of these embodiments, the at least one tool channel (e.g., the first tool channel 1122, the second tool channel 1124, etc.) may be omitted, and the first working instrument 1210 and/or the second working instrument 1220 may be slidably disposed directly within the at least one tool lumen (e.g., the first tool lumen 1112, the second tool lumen 1114, etc.)

With the working space 1151 formed, as described herein, the at least one tool channel (e.g., the first tool channel 1122, the second tool channel 1124, etc.), and/or the first working instrument 1210 and/or the second working instrument 1220, which may have a double curved configuration as described herein, accommodate for the shape of the working space 1151 so as not to sacrifice distances from the target tissue (e.g., the polyp 20, etc.) which would otherwise occur if the at least one tool channel (e.g., the first tool channel 1122, the second tool channel 1124, etc.), and/or the first working instrument 1210 and/or the second working instrument 1220, had a single curve configuration.

The first working instrument 1210, which may include the grasping tool 1212, may be utilized to manipulate the clip 1182 within the working space 1151—for example, to releasably attach the clip 1182 (and/or the second clip 1186) to the target tissue (e.g., the polyp 20, etc.) of the body lumen 10 proximate the working space 1151. In some embodiments, the first working instrument 1210 and/or the grasping tool 1212 may be configured to and/or used to manipulate (e.g., apply tension to) the target tissue (e.g., the polyp 20, etc.) of the body lumen 10 proximate the working space 1151, in place of and/or in conjunction with the clip 1182 and the filament 1180 (and/or the second clip 1186 and the second filament 1184), while the second working instrument 1220 resects, ablates, cauterizes, etc. the target tissue (e.g., the polyp 20, etc.) from the body lumen 10. Other working instruments for removal of the target tissue can also be utilized. Additionally, in some embodiments, a single tool channel may be utilized and an additional working instrument (e.g., a grasper, a dissector, etc.) may be inserted through a working channel (lumen) of the endoscope.

Figure 12:
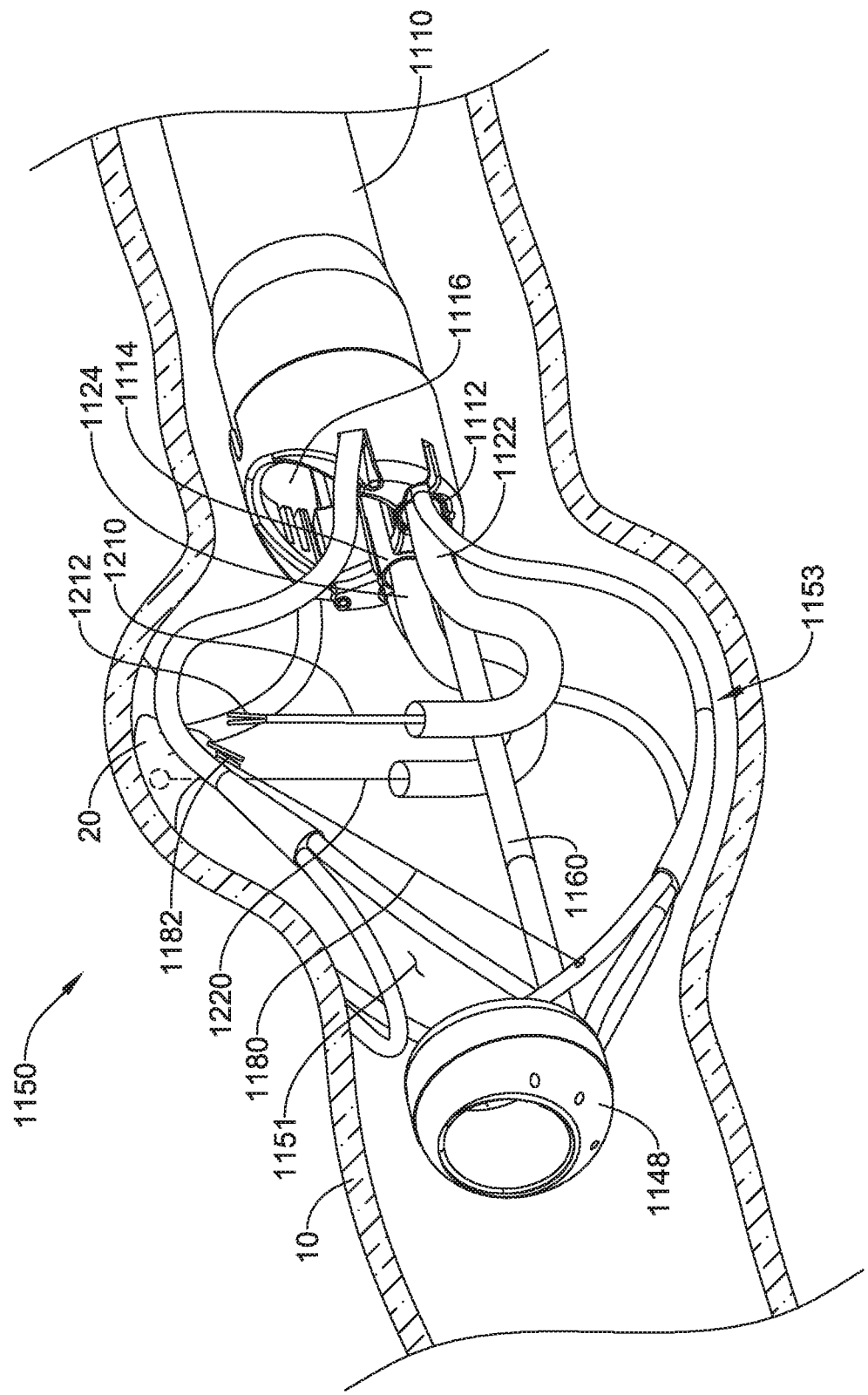

After releasably attaching the clip 1182 (and/or the second clip 1186) to the target tissue (e.g., the polyp 20, etc.), tension may be applied to the filament 1180 (and/or the second filament 1184) in order to retract the target tissue (e.g., the polyp 20, etc.), as shown in FIG. 12. Retraction of the target tissue (e.g., the polyp 20, etc.) during a procedure may result in a cleaner cut (in embodiments where cutting or resection occurs) and/or improved access to and/or around the target tissue (e.g., the polyp 20, etc.) still attached to the body lumen 10. For example, retraction of the target tissue (e.g., the polyp 20, etc.) may move the target tissue (e.g., the polyp 20, etc.) out of the way to prevent interference with the first working instrument 1210 and/or the second working instrument 1220. As seen in FIG. 12 for example, in some embodiments, the target tissue (e.g., the polyp 20, etc.) may be pulled away from the wall of the body lumen 10 and/or laterally relative to the central longitudinal axis of the flexible multi-lumen catheter 1110, thereby permitting a working instrument (e.g., the second working instrument 1220, for example) to access the wall of the body lumen 10 "behind" the target tissue (e.g., the polyp 20, etc.) that is under tension and/or retraction.

In some embodiments, after removal of the target tissue (e.g., the polyp 20, etc.) from the body lumen 10, the target tissue (e.g., the polyp 20, etc.) may be placed within the cover 1170 for removal from the body. In at least some embodiments, the clip 1182 and/or the second clip 1186 may assist in holding the target tissue (e.g., the polyp 20, etc.) as the target tissue (e.g., the polyp 20, etc.) is captured within the cover 1170, and/or may assist in retaining the target tissue (e.g., the polyp 20, etc.) within the cover 1170. In some embodiments, the stiffening actuator can be moved, translated, etc. to return the retractor system 1150 and/or the support beam 1160 to a more flexible configuration, if desired. The first working instrument 1210 and the second working instrument 1220 may be withdrawn back into the at least one tool lumen (e.g., the first tool lumen 1112, the second tool lumen 1114, etc.) within the flexible multi-lumen catheter 1110. The at least one tool channel (e.g., the first tool channel 1122, the second tool channel 1124, etc.) may be withdrawn into the at least one tool lumen (e.g., the first tool lumen 1112, the second tool lumen 1114, etc.) within the flexible multi-lumen catheter 1110. The retractor system actuator may be moved, translated, etc. to return the plurality of support elements 1153 (e.g., the first support element 1152, the second support element 1154, the third support element 1156, the fourth support element 1158, etc.) to the collapsed delivery configuration of FIG. 9 for removal of the system 1100, the flexible multi-lumen catheter 1110, etc. from the body lumen 10. The string or suture associated with the cover 1170 is then tensioned to close the cover 1170, thereby forming a closed bag to encapsulate the removed target tissue (e.g., the polyp 20, etc.). In some embodiments, a switch or locking element may be moved to a securing position to lock the string or suture and thereby maintain the cover 1170 as a closed bag. The flexible multi-lumen catheter 1110 may then be removed from the body lumen 10 with the removed target tissue (e.g., the polyp 20, etc.) protected (encapsulated) within the cover 1170.

The materials that can be used for the various components of the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc. (and/or other systems disclosed herein) and the various elements thereof disclosed herein may include those commonly associated with medical devices. For simplicity purposes, the following discussion makes reference to the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc. However, this is not intended to limit the devices and methods described herein, as the discussion may be applied to other elements, members, components, or devices disclosed herein, such as, but not limited to, the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc. and/or elements or components thereof.

In some embodiments, the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc., and/or components thereof and/or associated therewith (such as, but not limited to, the tubing 1136, the one-way stopcock 1138, the proximal port 1142, the removable cover 1144, the first support element 1152, the second support element 1154, the upper bridge member 1155, the third support element 1156, the lower bridge member 1157, the fourth support element 1158, the tubular elements 1159a/b, the tubular elements 1161a/b, etc.), may be made from a metal, metal alloy, polymer (some examples of which are disclosed herein), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum, platinum iridium alloys, platinum enriched stainless steel, and/or other platinum alloys; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc. to achieve the same result.

In some embodiments, a degree of Magnetic Resonance Imaging (MM) compatibility is imparted into the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc. For example, the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc., and/or components or portions thereof, may be made of a material that does not substantially distort the image and create substantial artifacts (e.g., gaps in the image). Certain ferromagnetic materials, for example, may not be suitable because they may create artifacts in an MM image. The system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system 1100, the flexible multi-lumen catheter 1110, the first tool channel 1122, the second tool channel 1124, the handle housing 1130, the at least one locking mechanism 1133, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the filament 1180, the clip 1182, the second filament 1184, the second clip 1186, the pull tab 1190, the second pull tab 1194, the spring 1196, the first working instrument 1210, the grasping tool 1212, the second working instrument 1220, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the system 1100, the flexible multi-lumen catheter 1110, the first tool channel 1122, the second tool channel 1124, the handle housing 1130, the proximal coupler cap 1140, the distal coupler cap 1148, the retractor system 1150, the plurality of support elements 1153, the support beam 1160, the outer tubular shaft 1163, the second outer tubular shaft 1167, the outer tubular shaft 1169, the cover 1170, the first working instrument 1210, the grasping tool 1212, the second working instrument 1220, etc. and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A system for performing minimally invasive procedures in a working space in a body lumen, the system comprising:
    a flexible catheter having a plurality of lumens extending from a handle housing to a distal end of the flexible catheter, wherein the plurality of lumens includes:
        a main lumen configured to receive an endoscope having a working channel; and
        at least one tool lumen;
    a first working instrument slidably disposed within a first tool lumen of the at least one tool lumen or the working channel of the endoscope;
    a retractor system disposed at the distal end of the flexible catheter, configured to shift between a delivery configuration and an expanded configuration, wherein in the expanded configuration, the retractor system extends radially outwardly and is capable of expanding the working space in the body lumen; and
    a first filament extending from the retractor system, when the retractor system is in the expanded configuration, to a clip, the clip being manipulatable by the first working instrument to engage tissue of the body lumen.

2. The system of claim 1, wherein the first working instrument includes a grasping tool.

3. The system of claim 1, wherein the clip is configured to releasably attach to tissue of the body lumen proximate the working space.

4. The system of claim 3, wherein tension applied to the first filament retracts the clip at an angle relative to a central longitudinal axis of the flexible catheter.

5. The system of claim 1, further comprising a tension-inducing element disposed at a proximal end of the filament.

6. The system of claim 5, wherein the tension-inducing element is a weight, a spring, or a pull tab.

7. The system of claim 1, further comprising a second filament extending from the retractor system, when the retractor system is in the expanded configuration, to a second clip, the second clip being manipulatable to engage tissue of the body lumen.

8. The system of claim 1, further comprising a second working instrument slidably disposed within the first tool lumen, a second tool lumen of the at least one tool lumen, or the working channel of the endoscope.

9. The system of claim 8, wherein the second working instrument is configured to manipulate the second filament and the second clip to engage tissue of the body lumen.

10. The system of claim 1, wherein the position of the first filament is variable with respect to the flexible catheter.

11. A system for performing minimally invasive procedures in a working space in a body lumen, the system comprising:
    a flexible catheter;
    a first working instrument disposed within the flexible catheter;
    a plurality of support elements extending from the distal end of the flexible catheter, the plurality of support elements being configured to shift between a delivery configuration and an expanded configuration, wherein in the expanded configuration, the plurality of support elements extend radially outwardly to expand the working space within the body lumen; and
    a first filament extendable from at least one of the plurality of support elements which may be adjusted to vary the location of the filament longitudinally relative to the flexible catheter.

12. The system of claim 11, wherein:
    the first working instrument is disposed in a first tool channel slidably disposed within the flexible catheter; and
    the first tool channel has a distal portion movable from a first position aligned with a longitudinal axis of the catheter when the distal portion of the first tool channel is disposed within the catheter, to an angled position with respect to the longitudinal axis of the catheter when the distal portion of the first tool channel is advanced out of the catheter.

13. The system of claim 12, wherein a distal end of the first tool channel opens laterally relative to the longitudinal axis of the catheter when the distal portion of the first tool channel is in the angled position.

14. The system of claim 11, further comprising a second filament extendable from at least one of the plurality of support elements at a variable location relative to the flexible catheter.

15. The system of claim 11, wherein the first filament extends to a clip, the clip being manipulatable by the first working instrument to grasp target tissue proximate the working space, the system further comprising a second working instrument configured to manipulate the target tissue.

16. A system for performing minimally invasive procedures in a working space in a body lumen, the system comprising:
   a flexible catheter having a plurality of lumens extending from a handle housing to a distal end of the flexible catheter;
   a first working instrument disposed within one of the plurality of lumens;
   a retractor system extending from the plurality of lumens at the distal end of the flexible catheter configured to shift between a delivery configuration and an expanded configuration, wherein in the expanded configuration, the retractor system expands radially outwardly and is capable of expanding the working space in the body lumen; and
   at least one filament extendable from the retractor system, when the retractor system is in the expanded configuration, the retractor system being adjustable to vary the position of the filament with respect to the distal end of the flexible catheter.

17. The system of claim 16, wherein the retractor system comprises at least one tubular shaft having a lumen extending from the handle housing to an opening through a side wall of the tubular shaft proximate the working space, wherein the opening through the side wall of the at least one tubular shaft is a longitudinally-oriented slot, and the at least one tubular shaft includes an outer tubular shaft slidably disposed over the at least one tubular shaft such that the filament exits the lumen of the at least one tubular shaft at a variable location along the longitudinally-oriented slot as determined by a distal end of the outer tubular shaft.

18. The system of claim 16, further comprising a second filament extendable from the retractor system at variable locations with respect to the distal end of the flexible catheter.

19. The system of claim 16, wherein the at least one filament comprises first and second filaments extending from the retractor system each at a variable location relative to the flexible catheter.

20. The system of claim 16, wherein the at least one filament extends to a clip, the clip being manipulatable by the first working instrument to grasp target tissue proximate the working space, the system further comprising a second working instrument configured to manipulate the target tissue.

* * * * *